United States Patent
Grace

(10) Patent No.: US 10,758,308 B2
(45) Date of Patent: Sep. 1, 2020

(54) CONTROLLER TO SELECT OPTICAL CHANNEL PARAMETERS IN A CATHETER

(71) Applicant: The Spectranetics Corporation, Colorado Springs, CO (US)

(72) Inventor: Kenneth P. Grace, Woodland Park, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 2054 days.

(21) Appl. No.: 13/826,053

(22) Filed: Mar. 14, 2013

(65) Prior Publication Data

US 2014/0276690 A1 Sep. 18, 2014

(51) Int. Cl.
*A61B 18/24* (2006.01)
*A61B 5/00* (2006.01)

(52) U.S. Cl.
CPC ............ *A61B 18/24* (2013.01); *A61B 5/0059* (2013.01); *A61B 5/6852* (2013.01); *A61B 5/0066* (2013.01); *A61B 5/0071* (2013.01); *A61B 5/0075* (2013.01); *A61B 5/4836* (2013.01)

(58) Field of Classification Search
CPC ..... A61B 18/24; A61B 5/0059; A61B 5/5852; A61B 5/0055; A61B 5/0071; A61B 5/4836; A61B 5/0075
USPC ..................................... 606/2–19; 607/88–89
See application file for complete search history.

(56) References Cited

U.S. PATENT DOCUMENTS

| | | | |
|---|---|---|---|
| 4,053,845 A | 10/1977 | Gould | |
| 4,641,912 A | 2/1987 | Goldenberg | |
| 4,669,465 A | 6/1987 | Moore et al. | |
| 4,686,979 A | 8/1987 | Gruen et al. | |
| 4,732,448 A | 3/1988 | Goldenberg | |
| 4,747,405 A | 5/1988 | Leckrone | |
| 4,769,005 A | 9/1988 | Ginsburg et al. | |
| 4,784,132 A | 11/1988 | Fox et al. | |
| 4,788,975 A | 12/1988 | Shturman et al. | |

(Continued)

FOREIGN PATENT DOCUMENTS

| | | |
|---|---|---|
| EP | 0211984 B2 | 3/1987 |
| EP | 2319404 B1 | 5/2011 |

(Continued)

OTHER PUBLICATIONS

Advisory Action issued in U.S. Appl. No. 12/337,232, dated Aug. 8, 2013, 3 pages.

(Continued)

*Primary Examiner* — Carl H Layno
*Assistant Examiner* — Dacheng Xie

(57) ABSTRACT

A system can include a microprocessor executable controller configured, based on one or more of total fiber active area of a laser catheter, imaging information regarding the target and/or non-target endovascular structure(s), target endovascular structure characterization information, current location and/or orientation of a distal tip of the laser catheter, and area of contact of the distal tip with the target and/or non-target endovascular structure to select at least one of a fiber active area for each optical channel, a number of optical channels, a configuration of fibers in an optical channel, an optical channel to be irradiated, and an ordering of optical channel irradiation.

9 Claims, 10 Drawing Sheets

(56) References Cited

U.S. PATENT DOCUMENTS

| | | | |
|---|---|---|---|
| 4,799,754 A | 1/1989 | Goldenberg | |
| 4,807,620 A | 2/1989 | Strul et al. | |
| 4,830,460 A | 5/1989 | Goldenberg | |
| 4,844,062 A | 7/1989 | Wells | |
| 4,848,336 A | 7/1989 | Fox et al. | |
| 4,850,686 A | 7/1989 | Morimoto et al. | |
| 4,913,142 A * | 4/1990 | Kittrell | A61B 1/00096 606/15 |
| 4,919,508 A * | 4/1990 | Grace | G02B 6/4296 385/56 |
| 4,924,863 A | 5/1990 | Sterzer | |
| 4,925,265 A | 5/1990 | Rink et al. | |
| 5,016,964 A | 5/1991 | Donnelly | |
| 5,024,234 A | 6/1991 | Leary et al. | |
| 5,026,366 A | 6/1991 | Leckrone | |
| 5,029,588 A | 7/1991 | Yock et al. | |
| 5,034,010 A | 7/1991 | Kittrell et al. | |
| 5,040,548 A | 8/1991 | Yock | |
| 5,041,108 A | 8/1991 | Fox et al. | |
| 5,047,952 A | 9/1991 | Kramer et al. | |
| 5,154,680 A | 10/1992 | Drzewiecki et al. | |
| 5,165,897 A | 11/1992 | Johnson | |
| 5,188,632 A | 2/1993 | Goldenberg | |
| 5,207,672 A | 5/1993 | Roth et al. | |
| 5,217,454 A | 6/1993 | Khoury | |
| 5,243,546 A | 9/1993 | Maggard | |
| 5,250,045 A | 10/1993 | Bohley | |
| 5,263,953 A | 11/1993 | Bagby | |
| 5,267,341 A | 11/1993 | Shearin | |
| 5,300,085 A | 4/1994 | Yock | |
| 5,304,171 A | 4/1994 | Gregory et al. | |
| 5,318,032 A | 6/1994 | Lonsbury et al. | |
| 5,350,375 A | 9/1994 | Deckelbaum et al. | |
| 5,350,377 A | 9/1994 | Winston et al. | |
| 5,350,395 A | 9/1994 | Yock | |
| 5,352,197 A | 10/1994 | Hammersmark et al. | |
| 5,377,683 A | 1/1995 | Barken | |
| 5,400,428 A | 3/1995 | Grace | |
| 5,415,653 A | 5/1995 | Wardle et al. | |
| 5,423,740 A | 6/1995 | Sullivan et al. | |
| 5,425,355 A | 6/1995 | Kulick | |
| 5,429,604 A | 7/1995 | Hammersmark et al. | |
| 5,429,617 A | 7/1995 | Hammersmark et al. | |
| 5,440,664 A | 8/1995 | Harrington et al. | |
| 5,451,233 A | 9/1995 | Yock | |
| 5,456,680 A | 10/1995 | Taylor et al. | |
| 5,464,395 A | 11/1995 | Faxon et al. | |
| 5,470,330 A | 11/1995 | Goldenberg et al. | |
| 5,483,080 A | 1/1996 | Tam | |
| 5,484,433 A | 1/1996 | Taylor et al. | |
| 5,492,131 A | 2/1996 | Galel | |
| 5,514,128 A | 5/1996 | Hillsman et al. | |
| 5,536,242 A | 7/1996 | Willard et al. | |
| 5,571,151 A | 11/1996 | Gregory | |
| 5,573,531 A | 11/1996 | Gregory | |
| 5,623,940 A | 4/1997 | Daikuzono | |
| 5,643,251 A | 7/1997 | Hillsman et al. | |
| 5,649,923 A | 7/1997 | Gregory et al. | |
| 5,657,760 A | 8/1997 | Ying et al. | |
| 5,722,972 A | 3/1998 | Power et al. | |
| 5,755,714 A | 5/1998 | Murphy-Chutorian | |
| 5,792,118 A | 8/1998 | Kurth et al. | |
| 5,800,350 A | 9/1998 | Coppleson et al. | |
| 5,803,083 A | 9/1998 | Buck et al. | |
| 5,807,377 A | 9/1998 | Madhani et al. | |
| 5,817,144 A | 10/1998 | Gregory | |
| 5,824,026 A | 10/1998 | Diaz | |
| 5,830,209 A | 11/1998 | Savage et al. | |
| 5,836,946 A | 11/1998 | Diaz et al. | |
| RE36,104 E | 2/1999 | Solar | |
| 5,891,133 A | 4/1999 | Murphy-Chutorian | |
| 5,938,609 A | 8/1999 | Pomeranz | |
| 5,976,124 A | 11/1999 | Reiser | |
| 5,986,643 A | 11/1999 | Harvill et al. | |
| 5,989,243 A | 11/1999 | Goldenberg | |
| 6,022,342 A | 2/2000 | Mukherjee | |
| 6,033,402 A | 3/2000 | Tu et al. | |
| 6,036,715 A | 3/2000 | Yock | |
| 6,056,743 A | 5/2000 | Ellis et al. | |
| 6,066,130 A | 5/2000 | Gregory et al. | |
| 6,117,128 A | 9/2000 | Gregory | |
| 6,231,563 B1 | 5/2001 | White et al. | |
| 6,287,297 B1 | 9/2001 | Woodruff et al. | |
| 6,290,668 B1 | 9/2001 | Gregory et al. | |
| 6,302,875 B1 | 10/2001 | Makower et al. | |
| 6,370,411 B1 | 4/2002 | Osadchy et al. | |
| 6,419,684 B1 | 7/2002 | Heisler et al. | |
| 6,432,115 B1 | 8/2002 | Mollenauer et al. | |
| 6,447,504 B1 | 9/2002 | Ben-Haim et al. | |
| 6,447,525 B2 | 9/2002 | Follmer et al. | |
| 6,458,098 B1 | 10/2002 | Kanesaka | |
| 6,539,132 B2 | 3/2003 | Ivtsenkov et al. | |
| 6,575,993 B1 | 6/2003 | Yock | |
| 6,597,829 B2 | 7/2003 | Cormack | |
| 6,733,495 B1 | 5/2004 | Bek et al. | |
| 6,743,208 B1 | 6/2004 | Coyle | |
| 6,792,390 B1 | 9/2004 | Burnside et al. | |
| 7,238,178 B2 | 7/2007 | Maschke | |
| 7,319,566 B2 | 1/2008 | Prince et al. | |
| 7,568,619 B2 | 8/2009 | Todd et al. | |
| 7,572,254 B2 | 8/2009 | Hebert et al. | |
| 7,846,153 B2 | 12/2010 | Hebert et al. | |
| 7,930,065 B2 | 4/2011 | Larkin et al. | |
| 7,959,608 B2 | 6/2011 | Nash et al. | |
| 7,988,633 B2 | 8/2011 | Hossack et al. | |
| 8,016,745 B2 | 9/2011 | Hassler et al. | |
| 8,016,748 B2 | 9/2011 | Mourlas et al. | |
| 8,050,739 B2 | 11/2011 | Eck et al. | |
| 8,100,893 B2 | 1/2012 | Dadisman | |
| 8,361,097 B2 | 1/2013 | Patel et al. | |
| 8,545,488 B2 | 10/2013 | Taylor et al. | |
| 8,628,519 B2 | 1/2014 | Taylor et al. | |
| 2001/0014805 A1 | 8/2001 | Burbank et al. | |
| 2002/0013572 A1 | 1/2002 | Berlin | |
| 2002/0026118 A1 | 2/2002 | Govari | |
| 2002/0045811 A1 | 4/2002 | Kittrell et al. | |
| 2002/0072661 A1 | 6/2002 | Wiesmann et al. | |
| 2002/0103459 A1 | 8/2002 | Sparks et al. | |
| 2002/0107445 A1 | 8/2002 | Govari | |
| 2002/0159685 A1 | 10/2002 | Cormack | |
| 2003/0032936 A1 | 2/2003 | Lederman | |
| 2003/0045798 A1 | 3/2003 | Hular et al. | |
| 2003/0078566 A1 | 4/2003 | Elliott et al. | |
| 2003/0204185 A1 | 10/2003 | Sherman et al. | |
| 2003/0219202 A1 | 11/2003 | Loeb et al. | |
| 2004/0010204 A1 | 1/2004 | Weber et al. | |
| 2004/0057659 A1 | 3/2004 | Baugh | |
| 2004/0059280 A1 | 3/2004 | Makower et al. | |
| 2004/0075919 A1 | 4/2004 | Diaz et al. | |
| 2004/0111016 A1 | 6/2004 | Casscells et al. | |
| 2004/0127889 A1 | 7/2004 | Zhang et al. | |
| 2004/0133154 A1 | 7/2004 | Flaherty et al. | |
| 2004/0162548 A1 | 8/2004 | Reiser | |
| 2005/0004453 A1 | 1/2005 | Tearney et al. | |
| 2005/0149176 A1 | 7/2005 | Heggestuen et al. | |
| 2005/0203416 A1 | 9/2005 | Angelsen et al. | |
| 2006/0020260 A1 | 1/2006 | Dover et al. | |
| 2006/0094930 A1 | 5/2006 | Sparks et al. | |
| 2006/0217695 A1 | 9/2006 | Debenedictis et al. | |
| 2006/0247532 A1 | 11/2006 | Ramanujam et al. | |
| 2007/0060879 A1 | 3/2007 | Weitzner et al. | |
| 2007/0106289 A1 | 5/2007 | O'Sullivan | |
| 2007/0115152 A1 | 5/2007 | Bjorklund et al. | |
| 2008/0019657 A1 | 1/2008 | Maitland et al. | |
| 2008/0058629 A1 | 3/2008 | Seibel et al. | |
| 2008/0106388 A1 | 5/2008 | Knight | |
| 2008/0108867 A1 | 5/2008 | Zhou | |
| 2008/0154296 A1 | 6/2008 | Taylor et al. | |
| 2009/0177095 A1 | 7/2009 | Aeby et al. | |
| 2009/0203989 A1 | 8/2009 | Burnside et al. | |
| 2010/0114081 A1 | 5/2010 | Keeler et al. | |
| 2010/0152717 A1 | 6/2010 | Keeler | |
| 2010/0168569 A1 | 7/2010 | Sliwa et al. | |
| 2010/0177309 A1 | 7/2010 | Scaiano et al. | |

(56) References Cited

U.S. PATENT DOCUMENTS

| | | | |
|---|---|---|---|
| 2010/0200076 A1* | 8/2010 | Hieb | A61M 5/16827 137/15.04 |
| 2011/0160681 A1 | 6/2011 | Dacey et al. | |
| 2011/0196291 A1 | 8/2011 | Vischer et al. | |
| 2011/0224649 A1 | 9/2011 | Duane et al. | |
| 2011/0270091 A1 | 11/2011 | Hossack et al. | |
| 2012/0181331 A1 | 7/2012 | Beden et al. | |
| 2012/0253360 A1 | 10/2012 | White et al. | |
| 2012/0302828 A1 | 11/2012 | Toledo-Crow et al. | |
| 2013/0131579 A1 | 5/2013 | Mantell et al. | |
| 2013/0253490 A1 | 9/2013 | Bitzer et al. | |
| 2013/0338500 A1 | 12/2013 | Taylor et al. | |
| 2014/0114298 A1 | 4/2014 | Taylor et al. | |
| 2014/0275982 A1 | 9/2014 | Hendrick et al. | |
| 2014/0276603 A1 | 9/2014 | Magee et al. | |
| 2014/0276689 A1 | 9/2014 | Grace | |
| 2015/0011843 A1 | 1/2015 | Toth et al. | |
| 2015/0141768 A1 | 5/2015 | Yu et al. | |

FOREIGN PATENT DOCUMENTS

| | | |
|---|---|---|
| GB | 2208807 A | 4/1989 |
| WO | 1998019614 A1 | 5/1998 |
| WO | WO0057228 A2 | 9/2000 |
| WO | 2010042249 A4 | 8/2010 |

OTHER PUBLICATIONS

European Search Report issued in EP Application No. 05796879.4 dated Mar. 6, 2008, 7 pages.
European Search Report issued in EP Application No. 08010688.3. dated Feb. 17, 2009, 6 pages.
Final Official Action for U.S. Appl. No. 12/337,232 dated Apr. 23, 2013, 11 pages.
Grundfest, Warren S., MD, et al., "Laser Ablation of Human Atherosclerotic Plaque Without Adjacent Tissue Injury," JACC vol. 5, No. 4, (Apr. 1985), pp. 929-933.
International Preliminary Report on Patentability issued in PCT/US2009/066133, dated Jun. 21, 2011, 8 pages.
International Search Report and Written Opinion issued in PCT/2014/019258, dated Aug. 8, 2014, 21 pages.
International Search Report and Written Opinion issued in PCT/2014/019283, dated Jun. 20, 2014, 15 pages.
International Search Report and Written Opinion issued in PCT/2014019278, dated May 7, 2014, 14 pages.
International Search Report and Written Opinion issued in PCT/US2005/033029, dated Oct. 3, 2006, 1 page.
International Search Report and Written Opinion issued in PCT/US2009/066133, dated Jan. 26, 2010, 8 pages.
Notice of Allowance for U.S. Appl. No. 12/649,759 dated May 16, 2013, 12 pages.
Notice of Allowance for U.S. Appl. No. 11/228,845 dated Jun. 5, 2009, 8 pages.
Notice of Allowance for U.S. Appl. No. 12/406,807 dated Aug. 2, 2010, 7 pages.
Notice of Alowance for U.S. Appl. No. 12/337,232 dated Sep. 6, 2013, 11 pages.
Official Action for U.S. Appl. No. 11/228,845 dated Jan. 12, 2009, 13 pages.
Official Action for U.S. Appl. No. 11/228,845 dated Sep. 3, 2008, 10 pages.
Official Action for U.S. Appl. No. 12/337,232 dated Mar. 23, 2012, 9 pages.
Official Action for U.S. Appl. No. 12/337,232 dated Sep. 13, 2012, 10 pages.
Official Action for U.S. Appl. No. 12/649,759 dated Aug. 30, 2012, 11 pages.
Official Action for U.S. Appl. No. 12/649,759 dated Jul. 16, 2012, 9 pages. (Restriction Requirement).
Griffin et al. Calibration and Mapping of a Human Hand for Dexterous Telemanipulation; ASME IMECE Conference, 2000, 8 pages.
Hager-Ross et al. Quantifying the Independence of Human Finger Movements: Comparisons of Digits, Hands, and Movement Frequencies; The Journal of Neurosciences, vol. 20 No. 22, Nov. 15, 2000, pp. 8542-8550.
Hajjarian et al. Intravascular Laser Speckle Imaging Catheter for the Mechanical Evaluation of the Arterial Wall; Journal of Biomedical Optics vol. 16(2) Feb. 2011, 7 pages.
Hanke et al. Morphological Changes and Smooth Muscle Cell Proliferation After Experimental Excimer Laser Treatment; Circulation vol. 83, 1991 pp. 1380-1389.
Hattori et al. Invivo Raman Study of the Living Rat Esophagus and Stomach Using a Micro-Raman Probe Under an Endoscope; Applied Spectroscopy vol. 61, No. 6, 2007, 8 pages.
Hauser Deaths and Cardiovascular Injuries Due to Device-Assisted Implantable Cardioverter-Defibrillator and Pacemaker Lead Extraction; Eurospace vol. 12, 2010, pp. 395-401.
Henning et al. An in Vivo Strain Gage Study of Elongation of the Anterior Cruciate Ligament; The American Journal of Sports Medicine, vol. 13, No. 1m 1985, pp. 22-26.
Inmann et al. An Instrument Object for Evaluation of Lateral Hand Grasp During Functional Tasks; Journal of Medical Engineering & Technology, vol. 25. No. 5, Sep./Oct. 2001, pp. 207-211.
Insull the Pathology of Atherosclerosis; Plaque Development and Plaque Responses to Medical Treatment; The American Journal of Medicine, vol. 122, No. 1A, Jan. 2009, 12 pages.
Jagsi et al. Original Investigation: Residents Report on Adverse Events and Their Causes; Arch Intern Med/ vol. 163 Dec. 12-26, 2005 7 pages.
Johns et al. Determination of Reduced Scattering Coefficient of Biological Tissue From a Needle-Like Probe; Optics Express vol. 13, No. 13. Jun. 27, 2005 pp. 4828-4842.
Kahol et al. Effect of Fatigue on Psychomotor and Cognitive Skills; The.
Kane et al. A Traction Stress Sensor Array for Use in High-Resolution Robotic Tactile Imaging; Journal of Microelectromechanical Systems, vol. 9, No. 4, Dec. 2000, pp. 425-434.
Kang et al. A Carbon Nanotube Strain Sensor for Structural Health Monitoring; Smart Matter. Struct. vol. 15, 2006, pp. 737-748.
Karimov et al. A Carbon Nanotube-Based Pressure Sensor, Phys. Scr. 83, 2011, 5 pages.
Karsch et al. Percutaneous Coronary Excimer Laser Angioplasty Initial Clinical Results; The Lancet, Sep. 16, 1989 pp. 647-650.
Kennergren Excimer Laser Assisted Extraction of Permanent Pacemaker and ICD Leads: Present Experiences of a European Multi-Centre Study; European Journal of Cardio-Thoracic Surgery 15, 1990, pp. 856-860.
Khairy et al. Laser Lead Extraction in Adult Congenital Heart Disease; J. Cardiovasc Electrophysiol, vol. 18, 2006, pp. 507-511.
Khalil et al. Tissue Elasticity Estimation With Optical Coherence Elastography: Toward Mechanical Characterization of in Vivo Soft Tissue; Annals of Biomedical Engineering, vol. 33, No. 11, Nov. 2005, pp. 1631-1639.
Kochiadakis et al. The Role of Laser-Induced Fluorescence in Myocardial Tissue Characterization: An Experimental Invitro Study; Chest vol. 120, 2001, pp. 233-239.
Koulouris et al. Intravascular Lead Extractions: Tips and Tricks; Intech Open Science/Open Minds http//creativecommons.org/licenses/by/3.0, 2012 pp. 189-216.
Kremers et al. The National ICD Registry Report: Version 2.1 Including Leads and Pediatrics for Years 2010 and 2011; pp. 59-65.
Lathan et al. The Effects of Operator Spatial Perception and Sensory Feedback on Human-Robot Teleoperation Performance; Presence, vol. 11, No. 4, Aug. 2002, 368-377.
Levine et al. 2011 ACCF/AHA/SCAI Guideline for Percutaneous Coronary Intervention: Executive Summary; Journal of the American College of Cardiology vol. 58, No. 24, 2011, pp. 2250-2583.
Li et al. Strain and Pressure Sensing Using Single-Walled Carbon Nanotubes; Nanotechnology vol. 15, 2004, pp. 1493-1496.

(56) References Cited

OTHER PUBLICATIONS

Lieber et al. Sarcomere Length Determination Using Laser Diffraction: Effect of Beam and Fiber Diameter; Biophys J. vol. 45, May 1984, pp. 1007-1016.
Lipomi et al. Skin-Like Pressure and Strain Sensors Based on Transparent Elastic Films of Carbon Nanotubes; Nature Nanotechnology, vol. 6, Dec. 2011, pp. 788-792.
Maréchal, L. et al. "Measurement System for Gesture Characterization During Chest Physiotherapy Act on Newborn Babies Suffering from Bronchiolitis." Proceedings of the 29th Annual International Conference of the IEEE EMBS, Cité Internationale, Lyon, France. Aug. 23-26, 2007. pp. 5770-5773.
Maytin et al. Multicenter Experience With Extraction of the Sprint Fidelis Implantable Cardioverter-Defibrillator Lead; Journal of the American College of Cardiology vol. 56, No. 8, 2010, pp. 642-646.
Maytin et al. The Challenges of Transvenous Lead Extraction; Heart vol. 97, 2011, pp. 425-434.
Medtronic's Brochure; Implantable Pacemaker and Defibrillator Information; Apr. 2006, 2 pages.
Meier-Ewert et al. Endocardial Pacemaker or Defibrillator Leads With Infected Vegetations: A Single-Center Experience and Consequences of Transvenous Extraction; AM Heart Journal vol. 146, 2003, pp. 339-344/.
Menciassi et al. Force Sensing Microinstrument for Measuring Tissue Properties and Pulse in Microsurgery, IEEE/ASME Transactions on Mechatronics, vol. 8, No. 1, Mar. 2003, pp. 10-17.
Mishra et al. Fiber Grating Sensors in Medicine: Current and Emerging Applications; Sensors and Actualtors A, 167, 2011, pp. 279-290.
Missinne Flexible Miniature Shear Sensors for Prosthetics; SPIE Newsroom SPIE, May 13, 2013, 4 pages.
Missinne, Jeroen et al. "Embedded Flexible Optical Shear Sensor." IEEE Sensors 2010 Conference. 2010. pp. 987-990.
Mond et al. The Electrode-Tissue Interface: The Revolutionary Role of Steroid Elution; Pace vol. 15, Jan. 1992, pp. 95-107.
Moscato et al. A Micromachined Intensity-Modulated Fiber Optic Sensor for Strain Measurements: Working Principle and Static Calibration; 34th Annual International Conference of the IEEE EMBS, 2012, pp. 5790-5793.
Mujat et al.; Automated Algorithm for Breast Tissue Differentiation in Optical Coherence Tomogrpahy; Journal of Biomedical Optics 14(3), 2009, 9 pages.
Neuzil et al. Pacemaker and ICD Lead Extraction With Electrosurgical Dissection Sheaths and Standard Transvenous Extraction Systems: Results of a Randomized Trial; Europace 9 , 2007, pp. 98-104.
Nikonovas et al. The Application of Force-Sensing Resistor Sensors for Measuring Forces Developed by the Human Hand; Proc. Instn Mech Engrs. vol. 218 Part H, 2004, 9 pages.
Nilsson et al Near Infrared Diffuse Reflection and Laser-Induced Fluorescence Spectroscopy for Myocardial Tissue Characterization; Spectrochimica ACTA Part A 53, 1997, pp. 1901-1912.
Noble et al. High Energy Excimer Laser to Treat Coronary in-Stent Restenosis in an Under Expanded Stent; Catheter and Cardiovascular Interventions vol. 71, 2008, pp. 803-807.
Noonan et al. A Dual-Function Wheeled Probe for Tissue Viscoelastic Property Identification During Minimally Invasive Surgery; IEEE International Conference on Robotics and Automation, Apr. 10-14, 2007, 6 pages.
Okumura et al. A Systematic Analysis of in Vivo Contact Forces on Virtual Catheter Tip/Tissue Surface Contact During Cardiac Mapping and Intervention; J. Cardiovasc Electrophysiol, vol. 19, Jun. 2008, pp. 632-640.
Orengo et al. Characterization of Piezoresistive Sensors for Goniometric Glove in Hand Prostheses; Wireless VITAE, 2009 pp. 684-687.
Park et al. Exoskeletal Force-Sensing End-Effectors With Embedded Optical Fiber-Bragg Grating Sensors; IEEE Transactions on Robotics, vol. 25, No. 6, Dec. 2009, pp. 1319-1331.
Park et al. Fingertip Force Control With Embedded Fiber Bragg Grating Sensors; IEEE conference on Robotics and Automation, May 19-23, 2008, pp. 3431-3436.
Park et al. Force Sensing Robot Fingers Using Embedded Fiber Bragg Grating Sensors and Shape Deposition Manufacturing; ; IEEE International Conference on Robotics and Automation, Apr. 10-14, 2007, . pp. 1510-1516.
Parker et al. Advanced Imaging Catheter Gives Surgeons the Inside Picture; Brochure Jun. 12, 2013: https//www.llnl.gov/str/DaSilva.html.
Patterson et al. Time Resolved Reflectance and Transmittance for the Non-Invasive Measurement of Tissue Optical Properties; Applied Optics vol. 28, No. 12, Jun. 15, 1989 pp. 2331-2336.
Peracchia Surgical Education in the Third Millennium; Annuals of Surgery, vol. 234, No. 6. 2001. pp. 709-712.
Pettit et al. Dynamic Optical Properties of Collagen-Based Tissue During ARF Excimer Laser Ablation; Applied Optics vol. 32, No. 4 Feb. 1, 1993, pp. 488-493.
Piers et al. A Micro Optical Force Sensor for Force Feedback During Minimally Invasive Robotic Surgery; Elsevier Sensors and Actuators A 115, 2004, pp. 447-455.
Polygerinos et al. MRI-Compatible Fiber-Optic Force Sensors for Catheterization Procedures; IEEE Sensors Journal vol. 10 No. 10, Oct. 2010, pp. 1598-1608.
Post et al.; Outcome After Complete Percutaneous Removal of Infected Pacemaker Systems and Implantable Cardiac Defibrillators; Internal Medicine Journal 36, 2006, pp. 790-792.
Prasad et al. A Modular 2-DOF Force-Sensing Instrument for Laparoscopic Surgery; MICCAI 2003, LNCS 2878 pp. 279-286.
Puangmali et al. State-of-the Art in Force and Tactile Sensing for Minimally Invasive Surgery; IEEE Sensors Journal vol. 8, No. 4, Apr. 2008, pp. 371-381.
Rajan et al. Photonic Crystal Fiber Sensors for Minimally Invasive Surgical Devices; IEEE Transactions on Biomedical Engineering, vol. 59, No. 2, Feb. 2012, pp. 332-338.
Reiley et al. Review of Methods for Objective Surgical Skill Evaluation Surg Endosc, vol. 25, 2011 pp. 356-366.
Richards et al. Skills Evaluation in Minimally Invasive Surgery Using Force/Torque Signatures; Surg Endosc vol. 14, 2000, pp. 791-798.
Rinaldi et al. Determinants of Procedural Outcome of Chronically Implanted Pacemaker and Defibrillator Leads Using the Excimer Laser Sheath Heart.bmj.com, Dec. 5, 2012, 3 pages.
Rocha et al. Fluorescence and Reflectance Spectroscopy for Identification of Atherosclerosis in Human Carotid Arteries Using Principal Components Analysis; Photomedicine and Laser Surgery vol. 26, No. 4, 2008, pp. 329-335.
Rosen et al. Markov Modeling of Minimally Invasive Surgery Based on Tool/Tissue Interaction and Force/Torque Signatures for Evaluating Surgical Skills; IEEE Transactions on Biomedical Engineering, vol. 48, No. 5 May 2001, 13 pages.
Rovithakis Artificial Neural Networks for Discriminating Pathologic From Normal Peripheral Vascular Tissue; IEEE Transactions on Biomedical Engineering, vol. 48, No. 10, Oct. 2001 pp. 1088-1097.
Ruttmann et al. Transvenous Pacemaker Lead Removal Is Safe and Effective Even in Large Vegetations: An Analysis of 53 Cases of Pacemaker Lead Endocarditis; Pace vol. 26, Mar. 2006 pp. 231-236.
Sangpradit et al. Tissue Identification Using Inverse Finite Element Analysis of Rolling Indentation; 2009 IEEE International Conference on Robotics and Automation; Kobe, Japan, May 12, 17, 2009, 6 pages.
Schroeder et al. Visualizing Surgical Training Databases: Exploratory Visualization, Data Modeling, and Formative Feedback for Improving Skill Acquisition: IEEE Computer Graphics and Applications, 2011, 11 pages; DOI 10.1109/MCG.2012.67.
Seibold et al. Prototype of Instrument for Minimally Invasive Surgery With 6-Axis Force Sensing Capability ; Proceedings of the 2005 IEEE International Conference on Robotics and Automation, Apr. 2005, 6 pages.
Sensor-Response-Compressive Force versus CNT sensor readout Chart, 2 pages.
Shah et al. Evaluation of a New Catheter Sensor for Real-Time Measurement of Tissue Contact; Heart Rhythm, vol. 3, No. 5, Supplement, May 2006 pp. S75-S76.

(56) References Cited

OTHER PUBLICATIONS

Simone et al. A Low Cost Instrumented Glove for Extended Monitoring and Functional Hand Assessment; Journal of Neuroscience Methods 160, 2007 pp. 335-348.
Smith et al. Extraction of Transvenous Pacing and ICD Leads; Pace vol. 31 Jun. 2008 pp. 736-752.
Sohail et al. Management and Outcome of Permanent Pacemaker and Implantable Cardioverter-Defibrillator Infections; Journal of the American College of Cardiology, vol. 49, No. 18, 2007 pp. 1851-1859.
Sokollik et al. New Model for Skills Assessment and Training Progress in Minimally Invasive Surgery; Surg Endosc vol. 18, 2004, pp. 495-500.
Sosa et al. The Importance of Surgeon Experience for Clinical and Economic Outcomes From Thyroidectomy; Annals of Surgery vol. 228, No. 3 pp. 320-330.
Spectranetics User Manual VisiSheath Dilator Sheath, 2011, 112 Pages.
Spectranetics Vascular Intervention ELCA: Coronary Laser Atherectomy Catheter Brochure (2012), 3 pages.
Spectranetics X80 User Manual ELCA Coronary Laser Atherectomy Catheter. Mar. 2012, 16 pages.
SPI2006 Shear Sensor Brochure—Real-Time Surface Shear Sensing Application: Human Interface; Tactilus Technology, 2006, 1 page.
Sturman et al. A Survey of Glove-Based Input; Clumsy Intermediary Devices Constrain Our Interaction With Computers and Their Applications. Glove-Based Input Devices Let Us Apply Our Manual Dexterity to the Task: IEEE Computer Graphics & Applications, Jan. 1994. pp. 30-39.
Sun et al. A Sub-Millemetric, 0.25 Mn Resolution Fully Integrated Fiber-Optic Force Sensing Tool for Retinal Microsurgery; Int J Comput Assist Radiol Surg. vol. 4(4): Jun. 2009, pp. 383-390.
Takano et al. Changes in Coronary Plaque Color and Morphology by Lipid-Lowering Therapy With Atorvastatin: Serial Evaluation by Coronary Angioscopy; The Journal of the American College of Cardiology, vol. 42, No. 4, 2003 pp. 680-686.
Taroni et al. In Vivo Absorption and Scattering Spectroscopy of Biological Tissues; Photochem. Photobiol. Sci. vol. 2, 2003. pp. 124-129.
Turchin et al. Novel Algorithm of Processing Optical Coherence Tomography Images for Differentiation of Biological Tissue Pathologies; Journal of Biomedical Optics 10(6), Nov./Dec. 2005, 11 pages.
Turner et al. Development and Testing of a Telemanipulation System With Arm and Hand Motion; Accepted to 2000 ASME IMECE Symp. Haptic Interfaces, 2000, 7 pages.
Valdastri et al. Integration of a Miniaturized Triaxial Force Sensor in a Minimally Invasive Surgical Tool; IEEE Transactions on Biomedical Engineering, vol. 53, No. 11, Nov. 2006 pp. 2397-2400.
Van der Meer et al. Quantitative Optical Coherence Tomography of Arterial Wall Components; Lasers in Medical Science vol. 20, 2005, pp. 45-51.
Van der Meijden et al. The Valve of Haptic Feedback in Conventional and Robot-Assisted Minimal Invasive Surgery and Virtual Reality Training: A Current Review; Surg. Endosc vol. 23, 2009. pp. 1180-1190.
Van Leeuwen et al. Origin of Arterial Wall Dissections Induced by Pulsed Excimer and Mid-Infrared Laser Ablation in the Pigl; JACC vol. 19, No. 7, Jun. 1992, pp. 1610-1618.
Van Lindert et al. The Influence of Surgical Experience on the Rate of Intraoperative Aneurysm Rupture and Its Impact on Aneurysm Treatment Outcome; Surg Neurol vol. 56, 2001, pp. 151-158.
Wagner et al. The Role of Force Feedback in Surgery: Analysis of Blunt Dissection; Presented at the Tenth Symposium on Haptic Interfaces for Virtual Environment and Teleoperator Systems, Mar. 24, 25, 2002, 7 pages.
Walker et al. Surgical Safety Checklists: Do They Improve Outcomes?; British Journal of Anaesthesia, 2012, pp. 1-8.
Wang et al. Characterization of a Silicon=Based Shear-Force Sensor on Human Subjects; IEEE Trans Biomed Eng., 2002 1 page.
Wang et al. Miniature All-Silica Optical Fiber Pressure Sensor With an Ultrathin Uniform Diaphragm; Optics Express vol. 18, No. 9, Apr. 26, 2010 pp. 9006-9014.
Wang et al. Review: The Physiological and Computational Approaches for Atherosclerosis Treatment; IJCA-15372, 2012, 13 pages.
Wang, Lin et al. "Characterization of a Silicon-Based Shear-Force Sensor on Human Subjects." IEEE Transactions on Biomedical Engineering, vol. 49, No. 11. Nov. 2002. pp. 1340-1347.
Wazni et al. Lead Extraction in the Contemporary Setting: The Lexicon Study; Journal of the American College of Cardiology vol. 55, No. 6, 2010, pp. 579-586.
Weiss et al. Muscular and Postural Synergies of the Human Hand; J. Neurophysiol 92, 2004pp. 523-535.
Wilkoff et al. Transvenous Lead Extraction: Heart Rhythm Society Expert Consensus on Facilities, Training, Indications, and Patient Management; Heart Rhythm, vol. 6, No. 7, Jul. 2009, pp. 1086-1104.
U.S. Appl. No. 14/586,312, filed Dec. 30, 2014.
U.S. Appl. No. 14/586,529, filed Dec. 30, 2014.
U.S. Appl. No. 14/586,543, filed Dec. 30, 2014.
Wikipedia, Linear discriminant analysis, Dec. 21, 2013, http://en.wikipedia.org/wiki/Linear_discriminant_analysis.
Abeysinghe et. Al. A Novel MEMS Pressure Sensor Fabricated on an Optical Fiber; IEEE Photonics Technology Letters vol. 13. No. 9 Sep. 2001 pp. 993-995.
Agency for Healthcare Research and Quality Adjunctive Devices in PCI to Remove Thrombi or Protect Against Distal Embolization in Patients With ACS: A Clinician Research Summary; Effective Health Care Program; AHRQ Pub. No. 11 (12)-EHC089-3 May 2012 4 pages.
Arifler et. al. Light Scattering From Collagen Fiber Networks: Micro-Optical Properties of Normal and Neoplastic Stroma; Biophysical Journal vol. 92 May 2007, pp. 3260-3274.
Ashok et al. Raman Spectroscopy Sensor for Surgical Robotics—Instrumentation and Tissue Differentiation Algorithm Biomedical Optics and 3D Imaging OSA 2012 4 pages.
Bach et al., Design and Fabrication of 60-Gb/s InP-Based Monolithic Photoreceiver OEICs and Modules, IEEE Journal of Selected Topics in Quantum Electronics, vol. 8, No. 6, Nov. 1, 2002, 6 pgs.
Baddour et al. Update on Cardiovascular Implantation Electronic Device Infections and Their Management: A Scientific Statement From the American Heart Association Circulation 121: Jan. 2010, pp. 458-477.
Badr et al. The State of the Excimer Laser for Coronary Intervention in the Drug-Eluting Stent ERA Cardiovascular Revascularization Medicine 14, 2013, pp. 93-98.
Bann et al. Attitudes Towards Skills Examinations for Basic Surgical Trainees J. Clin Pract Jan. 2005, 59, 1. pp. 107-113.
Baztarrica et al. Transvenous Extraction of Pacemaker Leads in Infective Endocarditis With Vegetations ≥ 20MM: Our Experience; Clinl. Cardiol 35, 4, 2012 pp. 244-249.
Beauvoit et al. Contribution of the Mitochondrial Compartment to the Optical Properties of the Rat Liver: A Theoretical and Practical Approach Biophysical Journal vol. 67 Dec. 1994 pp. 2501-2510.
Beccai et al. Design and Fabrication of a Hybrid Silicon Three-Axial Force Sensor for Biomechanical Applications; Sensors and Actuators A 120, 2005, pp. 370-382.
Berkelman et al. A Miniature Microsurgical Instrument Tip Force Sensor for Enhanced Force Feedback During Robot-Assisted Manipulation; IEEE Transactions on Robotics and Automaton, vol. 19, No. 5, Oct. 2003, pp. 917-922.
Bilodeau et al. Novel Use of a High-Energy Excimer Laser Catheter for Calcified and Complex Coronary Artery Lesions Catheterization and Cardiovascular Interventions 62: 2004 pp. 155-161.
Bindig et al. Fiber-Optical and Microscopic Detection of Malignant Tissue by Use of Infrared Spectrometry Journal of Biomedical Optics vol. 7 No. 1 Jan. 2002 pp. 100-108.
Bishop et al. Paid Malpractice Claims for Adverse Events in Inpatient and Outpatient Settings; JAMA vol. 205 No. 23 Jun. 15, 2011, pp. 2427-2431.
Bittl et al. Meta-Analysis of Randomized Trials of Percutaneous Transluminal Coronary Angioplasty Versus Atherectomy, Cutting

(56) References Cited

OTHER PUBLICATIONS

Balloon Atherotomy, or Laser Angioplasty Journal of the American College of Cardiology vol. 43 No. 6 2004 pp. 936-942.
Bongiomi et al. Transvenous Removal of Pacing and Implantable Cardiac Defibrillating Leads Using Single Sheath Mechanical Dilatation and Multiple Venous Approaches; High Success Rate and Safety in More Than 200 Leads; European Heart Journal vol. 29, 2008, pp. 2886-2893.
Bracke et al. Pacemaker Lead Complications: When Is Extraction Appropriate and What Can We Learn From Published Data? Heart 2001 vol. 85 pp. 254-259.
Brennan et al. Analysis of Errors Reported by Surgeons at Three Teaching Hospitals, Surgery vol. 3, No. 6, 2003 pp. 614-621.
Britton Chance Optical Method; Annu Rev. Biophys. Chem vol. 20 1991 pp. 1-30.
Buch et al. Pacemaker and Defibrillator Lead Extraction; Circulation 2011:123 pp. 378-380.
Byrd et al. Clinical Study of the Laser Sheath for Lead Extraction: The Total Experience in the United States; Journal of Pacing and Clinical Electrophysiology, vol. 25 No. 5, May 2002 pp. 804-808.
Byrd et al. Intravascular Lead Extraction Using Locking Stylets and Sheaths; Pace vol. 13 Dec. 1990, pp. 1871-1875.
Candefjord et al. Combining Fibre Optic Raman Spectroscopy and Tactile Resonance Measurement for Tissue Characterization; Meas. Sci Technol. vol. 21, 2010 125801 8 pages.
Candinas et al. Postmortem Analysis of Encapsulation Around Long-Term Ventricular Endocardial Pacing Leads; Mayo Clin Proc. vol. 74, Feb. 1999, pp. 120-125.
Carlson et al. Motion Capture Measures Variability in Laryngoscopic Movement During Endotracheal Intubation: A Preliminary Report; 2012 Society for Simulation in Healthcare, vol. 7, No. 1, Aug. 2012 pp. 255-260.
Chan et al. Effects of Compression on Soft Tissue Optical Properties; IEEE Journal of Selected Topics in Quantum Electronics, vol. 2 No. 4, Dec. 1996 pp. 943-950.
Cheong et al. A Review of the Optical Properties of Biological Tissues; IEEE Journal of Quantum Electronics vol. 26, No. 12, Dec. 1990 pp. 2166-2185.
Chung, Kit Man. Advanced Fibre Bragg Grating and Microfibre Bragg Grating Fabrication Techniques; A Thesis Submitted in Partial Fulfillment of the Requirements for the Degree of Doctor of Philosophy, the Hong Kong Polytechnic University; Mar. 2012 (abstract of thesis/document attached; full printed version of thesis/document unavailable; entire online version of thesis/document available at http://repository.lib.polyu.edu.hk/jspui/handle/10397/5524).
Cruz et al. Internal Mammary Arterial Injury From Lead Extraction: A Clinically Subtle Yet Important Complication of Implantable Device Removal; Cardiology Research and Practice vol. 2011, Article ID 408640, (2011) 5 pages.
Da et al. Overview of the Vascular Interventional Robot; The International Journal of Medical Robotics and computer assisted surgery 2008;4: pp. 289-294.
Dallon et al. A Mathematical Model for Spatially Varying Extracellular Matrix Alighment; Siam J. Appl. Math. vol. 61, No. 2, 2000, pp. 506-527.
Deharo et al. Pathways for Training and Accreditation for Transvenous Lead Extraction: A European Heart Rhythm Association Position Paper; Europace 14 (2012) pp. 124-134.
Dipietro et al. Evaluaton of an Instrumented Glove for Hand-Movement Acquisition; Journal of Rehabilitation Research and Development vol. 40, No. 2, Mar./Apr. 2003, pp. 179-190.
Eichhorn et al. Carbon Nanotube Filled Composite Material Analysis Utilizing Nano and Conventional Testing Techniques; NIP & Digital Fabrication Conference, 2010 International Conference on Digital Printing Technologies. 5 Pages.
Eichhorn et al. Flexible Carbon Nanotube Composite Sensors for Medical Device Application; J. Med. Devices 7(2), 020943 (Jun. 11, 2013) (2 pages)Paper No. MED-13/1050; doi: 10.1115/1.4024311.
ELCA Coronary Laser Atherectomy Catheter Brochure, Spectranetics, 2012.
El-Sawah et al. A Prototype for 3-D Hand Tracking and Posture Estimation; IEEE Transactions on Instrumentation and Measurement, vol. 57, No. 8, Aug. 2008, pp. 1627-1636.
Endo et al. Clinical Utility of Intraprocedural Transesophagael Echocardiography During Transvenous Lead Extraction; Journal of the American Society of Echocardiography vol. 21 No. 7, Jul. 2008 pp. 862-867.
Epstein et al. Gross and Microscopic Pathological Changes Associated With Nonthoracotomy Implantable Defibrillator Lead; Circulation 1998:98: 1517-1524.
Erturk et al. Outcome of Surgery for Acromegaly Performed by Different Surgeons: Importance of Surgical Experience; Pituitary 8: 2005, pp. 93-97.
Esenaliev et al. Laser Ablation of Atherosclerotic Blood Vessel Tissue Under Various Irradiation Conditions; IEEE Transactions on Biomedical.
Esposito et al. Morphologic and Immunohistochemical Observations of Tissues Surrounding Retrieved Transvenous Pacemaker Leads; Wiley Periodicals, Inc. 2002, pp. 548-558.
Faber et al. Light Absorption of (Oxy-) Hemoglobin Assessed by Spectroscopic Optical Coherence Tomography; Optics Letters vol. 28, No. 16, Aug. 15, 2003 pp. 1436-1438.
Fanson et al. A System for Laparoscopic Surgery Ergonomics and Skills Evaluation; Journal of Endourology vol. 25, No. 7, Jul. 2011 pp. 1111-1114.
U.S. Appl. No. 09/947,171, filed Sep. 4, 2001, 71 pages.
FSR: Force Sensing Resistor Integration Guide and Evaluation Parts Catalog: 400 Series Evaluation Parts With Suggested Electrical Interfaces; Interface Electronics; Version 1.0 (90-45632 Rev. D), 26 pages.
Fung et al. A PMMA-Based Micro Pressure Sensor Chip Using Carbon Nanotubes as Sensing Elements; IEEE International Conference on Micro Electro Mechanical Systems, vol. 18, 2005 pp. 251-254.
Ghosh et al. Laser Lead Extraction: Is There a Learning Curve?; Pace, vol. 28; Mar. 2005 pp. 180-184.
Golzio et al. Prevention and Treatment of Lead Extraction Complications; Transvenous Lead Extraction; Springer-Verlag Italia 2011 pp. 129-136.
Wise et al. Evaluation of a Fiber Optic Glove for Semi-Automated Goniometric Measurements; Journal of Rehabilitation Research and Development vol. 27 No. 4, 1990, pp. 411-424.
Wollmann et al. Two Different Therapeutic Strategies in ICD Lead Defects: Additional Combined Lead Versus Replacement of the Lead; Journal of Cardiovascular Electrophysiology vol. 18, No. 11, Nov. 2007, pp. 1172-1177.
Yamamoto et al. Tissue Property Estimation and Graphical Display for Teleoperated Robot-Assisted Surgery; 2009 IEEE International Conference on Robotics and Automation, May 12, 17, 2009, 7 pages.
Yokoyama et al. Novel Contact Force Sensor Incorporated in Irrigated Radiofrequency Ablation Catheter Predicts Lesion Size and Incidence of Steam Pop and Thrombus Clinical Perspective; Circulation Arrhythmia and electrophysiology: Journal of the American Heart Association, Dec. 2008, pp. 353-362.
Yun et al. An Instrumented Glove for Grasp Specification in Virtual-Reality-Based Point and Direct Telerobotics; IEEE Transactions on Systems, Man, and Cybernetics—Bart B: Cybernetics, vol. 27, No. 5, Oct. 1997, pp. 835-846.
Zhan et al. Excess Length of Stay, Charges, and Mortality Attributable to Medical Injuries During Hospitalization; Journal of American Medical Association, vol. 290, No. 14, Oct. 8, 2003, pp. 1868-1874.
Extended European Search Report issued in European Patent Application 14773432.1, dated Oct. 4, 2016.

* cited by examiner

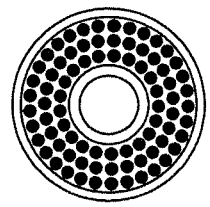
FIG.11
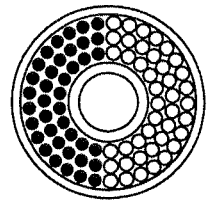 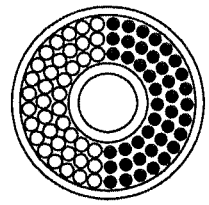
FIG.12A  FIG.12B
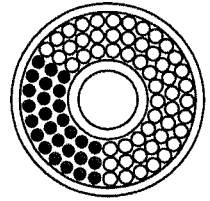 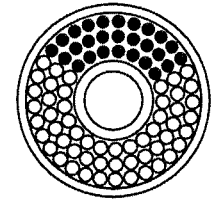 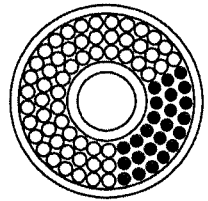
FIG.13A  FIG.13B  FIG.13C
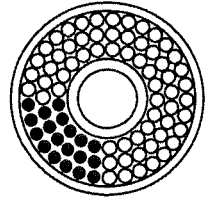 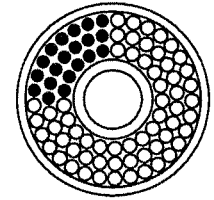 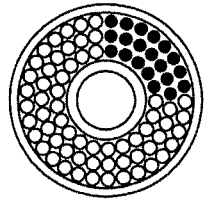 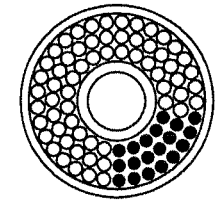
FIG.14A  FIG.14B  FIG.14C  FIG.14D

CONTROLLER TO SELECT OPTICAL CHANNEL PARAMETERS IN A CATHETER

FIELD

The disclosure relates generally to endovascular devices and particularly to laser catheters.

BACKGROUND

Laser energy can be transmitted through multiple optical fibers housed in a relatively flexible tubular catheter inserted into a body lumen, such as a blood vessel, ureter, fallopian tube, cerebral artery and the like to remove obstructions in the lumen. Catheters used for laser angioplasty and other procedures can have a central passage or tube which receives a guide wire inserted into the body lumen (e.g., vascular system) prior to catheter introduction. The guide wire facilitates the advancement and placement of the catheter to the selected portion(s) of the body lumen for laser ablation of tissue.

In designing a laser catheter, there are a number of considerations.

For example, laser energy should be controllably and selectively delivered onto single fibers or smaller sub-bundles of subsets of fibers that make up the total number of fibers that are incorporated into the device. This can reduce the overall impact of heat or acoustic shock that can damage tissue adjacent to the treatment site by dividing the transmitted laser energy into smaller packets. It can enable selective treating and targeting of specific zones encountered by the distal tip of the catheter by activating only the fibers required to heat those zones. It can reduce the overall power and energy requirements of the treatment laser by activating smaller portions of fibers in the catheter rather than activating all of the fibers simultaneously. When the instantaneous energy delivered by laser angioplasty catheters is maintained below an "adverse effect" threshold, while at the same time delivering the proper fluence values for tissue ablation, a significant reduction in the incidence of undesirable tissue damage can occur. Previous laser catheters able to energize controllably and selectively fibers used fairly complex scan systems including galvanometer scanners (open and closed loop), piezo type deflection devices, and other mechanical beam or coupler deflection systems. These types of systems typically require a fairly complex and expensive drive and control system. Often, diseased tissue is present in locations where only a portion of the laser catheter's distal tip is in contact with the diseased tissue. It may be desirable to activate only the portion of the distal tip in contact with the diseased tissue. Additionally, laser catheters are used to cut or ablate adhesions holding implanted objects in biological tissue. For safety reasons, it may be desirable to ablate only the tissue in contact with the laser delivery device tip and to avoid ablating tissue adjacent to the wall or artery to prevent perforation.

Notwithstanding these considerations, laser catheters typically energize all of the fibers simultaneously to achieve bulk ablation. Such fiber activation outputs energy from all fibers simultaneously. The resultant instantaneous energy required to achieve the fluence, or energy density values for ablation, can become high enough to induce undesirable tissue damage, including laser induced dissection.

SUMMARY

These and other needs are addressed by the various aspects, embodiments, and/or configurations of the present disclosure.

A method, in accordance with this disclosure, can include the step of selecting, by a microprocessor executable controller and based on one or more of total fiber active area of a laser catheter, imaging information regarding the target and/or non-target endovascular structure(s), target endovascular structure characterization information, current location and/or orientation of a distal tip of the laser catheter, and area of contact of the distal tip with the target and/or non-target endovascular structure at least one of a fiber active area for each optical channel, a number of optical channels, a configuration of fibers in an optical channel, an optical channel to be irradiated, and an ordering of optical channel irradiation.

A system, in accordance with this disclosure, can include a microprocessor executable controller configured, based on one or more of total fiber active area of a laser catheter, imaging information regarding the target and/or non-target endovascular structure(s), target endovascular structure characterization information, current location and/or orientation of a distal tip of the laser catheter, and area of contact of the distal tip with the target and/or non-target endovascular structure to select at least one of a fiber active area for each optical channel, a number of optical channels, a configuration of fibers in an optical channel, an optical channel to be irradiated, and an ordering of optical channel irradiation.

In accordance with the disclosure, a tangible, non-transient computer readable medium can include microprocessor executable instructions that, when executed, perform operations comprising selecting, based on one or more of total fiber active area of a laser catheter, imaging information regarding the target and/or non-target endovascular structure(s), target endovascular structure characterization information, current location and/or orientation of a distal tip of the laser catheter, and area of contact of the distal tip with the target and/or non-target endovascular structure at least one of a fiber active area for each optical channel, a number of optical channels, a configuration of fibers in an optical channel, an optical channel to be irradiated, and an ordering of optical channel irradiation.

The microprocessor executable controller can be configured to select the number of optical channels and fiber active area per optical channel to maintain a level of energy delivered by the irradiated optical channel below an adverse effect threshold but above a level to provide a proper fluence value for tissue ablation.

The microprocessor executable controller can be configured to select a first number of optical channels for a first catheter and a second number of optical channels for a second catheter, wherein the first and second numbers of optical channels are different, and wherein a first total fiber active area of the first catheter is different from a second total fiber active area of the second catheter.

The microprocessor executable controller can be configured to select the at least one of a fiber active area for each optical channel, a number of optical channels, a configuration of fibers in an optical channel, an optical channel to be irradiated, and an ordering of optical channel irradiation based on total fiber active area of the laser catheter.

The microprocessor executable controller can select the at least one of a fiber active area for each optical channel, a number of optical channels, a configuration of fibers in an optical channel, an optical channel to be irradiated, and an ordering of optical channel irradiation based on imaging information regarding the target and/or non-target endovascular structure(s), target endovascular structure characterization information, current location and/or orientation of a distal tip of the laser catheter, and area of contact of the distal tip with the target and/or non-target endovascular structure.

The disclosure can include a rotating optical member to receive a laser beam along an optical path and rotate to a selected position to redirect the laser beam from the optical path onto one or more selected optical fibers of the laser catheter, wherein the distal end of the laser catheter irradiates the target endovascular structure.

The present disclosure can provide a number of advantages depending on the particular aspect, embodiment, and/or configuration. Laser energy can be controllably and selectively delivered onto single fibers or smaller sub-bundles of subsets of fibers that make up the total number of fibers that are incorporated into the device. This can reduce the overall impact of heat or acoustic shock that can damage tissue adjacent to the treatment site by dividing the transmitted laser energy into smaller packets. It can enable selective treating and targeting of specific zones encountered by the distal tip of the catheter by activating only the fibers required to heat those zones. It can reduce the overall power and energy requirements of the treatment laser by activating smaller portions of fibers in the catheter rather than activating all of the fibers simultaneously. Activating portions of the distal tip of the catheter using the treatment laser or other diagnostic light source to probe the area of the lesion contact or tissue disease type and/or location to assess the best method or location of the fibers to be activated at the distal end for treatment. This can be accomplished using a simpler and relatively inexpensive beam deflection mechanism. By using rotating optics and rotational position monitoring using encoders or proximity sensors to fire the laser at the exact time the beam is incident on the target fiber or bundles of fibers, a much simpler multiplexed system can be provided. It can eliminate costly galvanometer scanners and amplifiers with closed loop position feedback electronics. A circular multi-fiber coupler can be fabricated easily. Controllable and selective fiber energizing can enable activating only the portion of the distal tip in contact with the diseased tissue. Additionally, it can ablate only the tissue in contact with the laser delivery device tip and avoid ablating tissue adjacent to the wall or artery to prevent perforation. It can avoid providing too much instantaneous energy and inducing undesirable tissue damage, including laser induced dissection. In other words, it can maintain the instantaneous energy delivered by laser angioplasty catheters below the "adverse effect" threshold, while at the same time delivering the proper fluence values for tissue ablation, thereby providing a significant reduction in the incidence of undesirable tissue damage should occur.

These and other advantages will be apparent from the disclosure.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

An "axicon" is an optical element that produces a line image lying along the axis from a point source of light; therefore, it has no definite focal length. An example is a lens with a weak conical surface on one face.

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

The terms "determine", "calculate" and "compute," and variations thereof, as used herein, are used interchangeably and include any type of methodology, process, mathematical operation or technique.

A "laser emitter" refers to an end portion of a fiber or an optical component that emits laser light from a distal end of the catheter towards a desired target, which is typically tissue.

A "catheter" is a tube that can be inserted into a body cavity, duct, lumen, or vessel, such as the vasculature system. In most uses, a catheter is a thin, flexible tube ("soft" catheter), though in some uses, it may be a larger, solid less flexible—but possibly still flexible—catheter ("hard" catheter).

"Coronary catheterization" is a generally minimally invasive procedure to access the coronary circulation and/or blood filled chambers of the heart using a catheter. It is performed for both diagnostic and interventional (treatment) purposes.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

"Electromagnetic radiation" or "EM radiation" or "EMR" is a form of energy emitted and absorbed by charged particles which exhibits wave-like behavior as it travels through space. EMR has both electric and magnetic field components, which stand in a fixed ratio of intensity to each other, and which oscillate in phase perpendicular to each other and perpendicular to the direction of energy and wave propagation. The electromagnetic spectrum, in order of increasing frequency and decreasing wavelength, consists of radio waves, microwaves, infrared radiation, visible light, ultraviolet radiation, X-rays and gamma rays.

A "lead" is a conductive structure, typically an electrically insulated coiled wire. The electrically conductive material can be any conductive material, with metals and intermetallic alloys common. The outer sheath of insulative material is biocompatible and biostable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "module" as used herein refers to any known or later developed hardware, software, firmware, artificial intelligence, fuzzy logic, or combination of hardware and software that is capable of performing the functionality associated with that element. Also, while the disclosure is presented in terms of exemplary embodiments, it should be appreciated that individual aspects of the disclosure can be separately claimed.

An "optical fiber" or "laser active fiber" is a flexible, transparent fiber made of an optically transmissive material, such as glass (silica) or plastic, that functions as a waveguide, or "light pipe", to transmit light between the two ends of the fiber.

A "surgical implant" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and/or configurations of the disclosure are possible utilizing, alone or in combination, one or more of the features set forth above or described in detail below.

BRIEF DESCRIPTION OF THE DRAWINGS

FIG. 11 depicts a first energizing mode;

FIGS. 12A-B depict a second energizing mode;

FIGS. 13A-C depict a third energizing mode; and

FIGS. 14A-D depict a fourth energizing mode.

DETAILED DESCRIPTION

Figure 2:
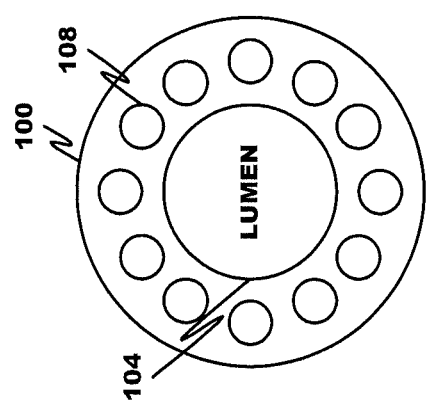
FIG. 2 depicts a distal tip of a lumenless laser catheter.
Figure 1:
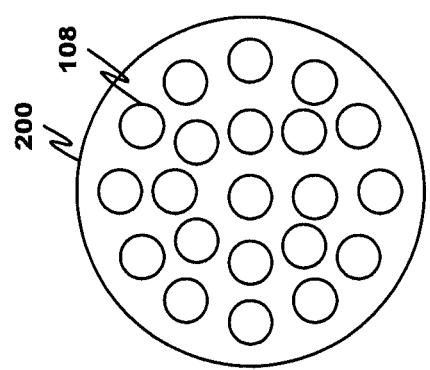
FIG. 1 depicts a distal tip of a laser catheter containing a lumen.

FIGS. 1 and 2 depict the working or distal ends of various known prior art laser catheters having plural optical fibers 324 embedded therein. FIG. 1 shows a flexible catheter 100 comprising a catheter lumen 104 to receive an implanted lead or guide wire (not shown) and plural laser emitters 108 positioned around the periphery or diameter of the catheter lumen 104. This type of catheter assembly is sold as a coronary laser atherectomy catheter by the Spectranetics Corporation under the tradenames ELCA™ and Turbo Elite™ (each of which is used for coronary intervention or catheterization such as recanalizing occluded arteries, changing lesion morphology, and facilitating stent placement) and as a laser sheath under the tradename SLSII™ and GlideLight™ (which is used for surgically implanted lead removal). FIG. 2 shows a flexible catheter 200 comprising plural laser emitters 108 packed into the distal end of the catheter. The number of rows of optical fibers and emitters located in the catheter and/or located concentrically around the lumen and the number of optical fibers and emitters in each row can vary by application and are not limited to the depicted configurations. The primary difference between the catheters in FIGS. 1 and 2 is the absence of a catheter lumen 104 in the catheter of FIG. 2.

Figure 3:
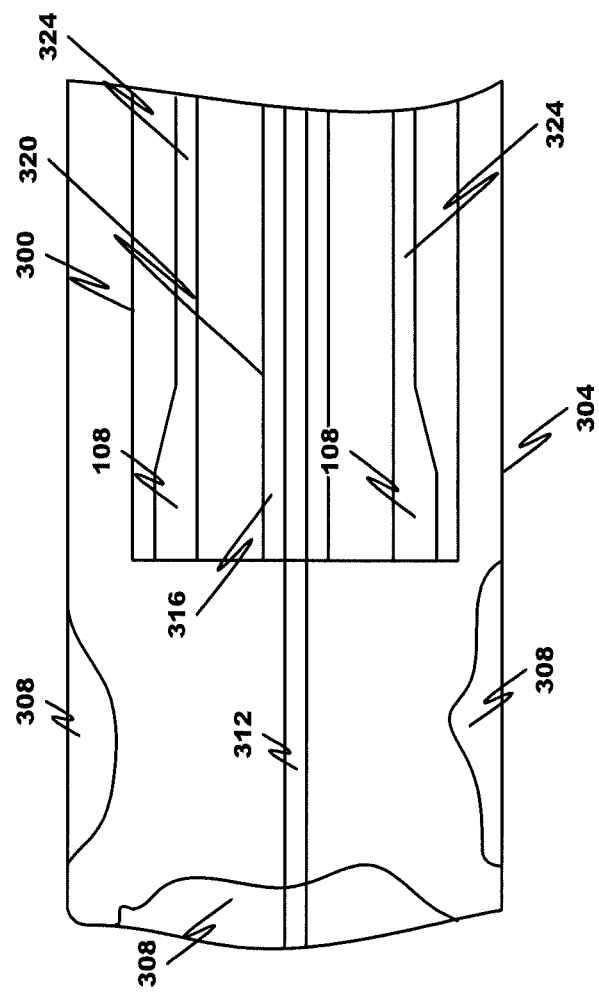
FIG. 3 is a cross-sectional view of the distal tip of FIG. 1 approaching target tissue or other endovascular structure.

Referring to FIG. 3, a laser ablation catheter 300 is positioned in a body lumen 304, such as a blood vessel, to remove a complete or partial occlusion 308. A guide wire 312 passes through the body lumen 304 and occlusion 308 on the one hand and the catheter lumen 316 formed by a substantially cylindrical inner catheter surface 320 on the other to guide the catheter to the occlusion 308. Laser emitters 108 are positioned at the distal end of the catheter to ablate the occlusion. Optical fiber 324 connects a corresponding emitter to the laser via the proximal end or coupler (FIG. 8).

Figure 8:
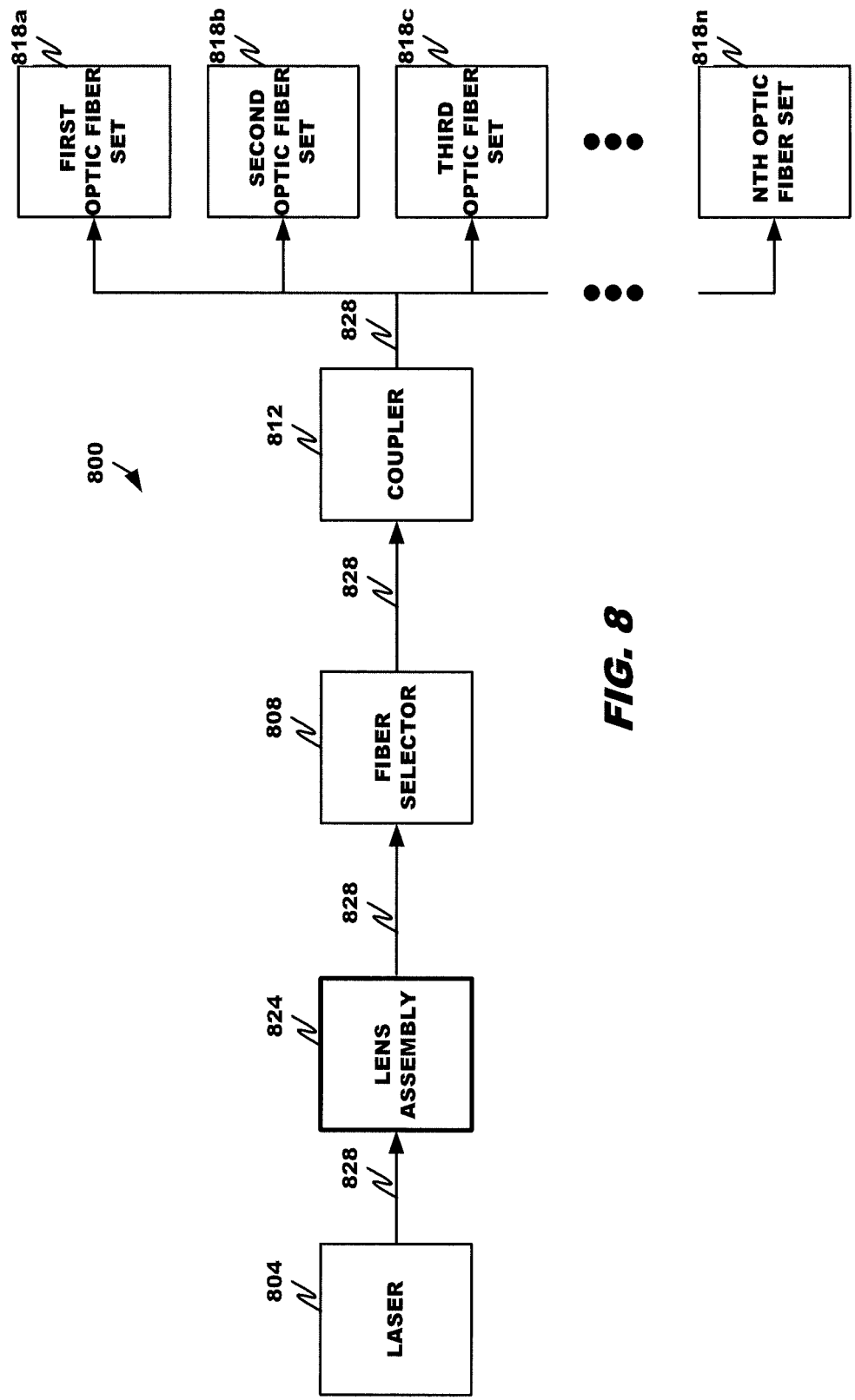
FIG. 8 depicts a multiplexing system according to an embodiment.

FIG. 8 depicts a laser assembly 800 including a laser 804, such as a low-temperature excimer laser operating in the ultraviolet spectrum at around 308 nm, a lens assembly 824 (which includes one or more lenses and/or filters), a fiber selector 808 to controllably and selectively energize fibers 108, a coupler 812 to couple to a proximal end of the laser catheter 300, and plural optical channels, each channel being represented by a corresponding first, second, third, . . . nth optic fiber set 818a-n. The laser 804 emits laser energy or beam 828, which is directed by the laser assembly 800 to the fiber selector 808. The fiber selector 808 directs the laser energy 828, through the coupler 812, and onto a selected one of the first, second, third, . . . nth optic fiber set 818a-n. As will be appreciated, the laser 804 can be the same for both treatment and diagnostic laser pulses or different lasers may be employed. When compared to treatment laser pulses, diagnostic laser pulses use lower power.

Figure 6:
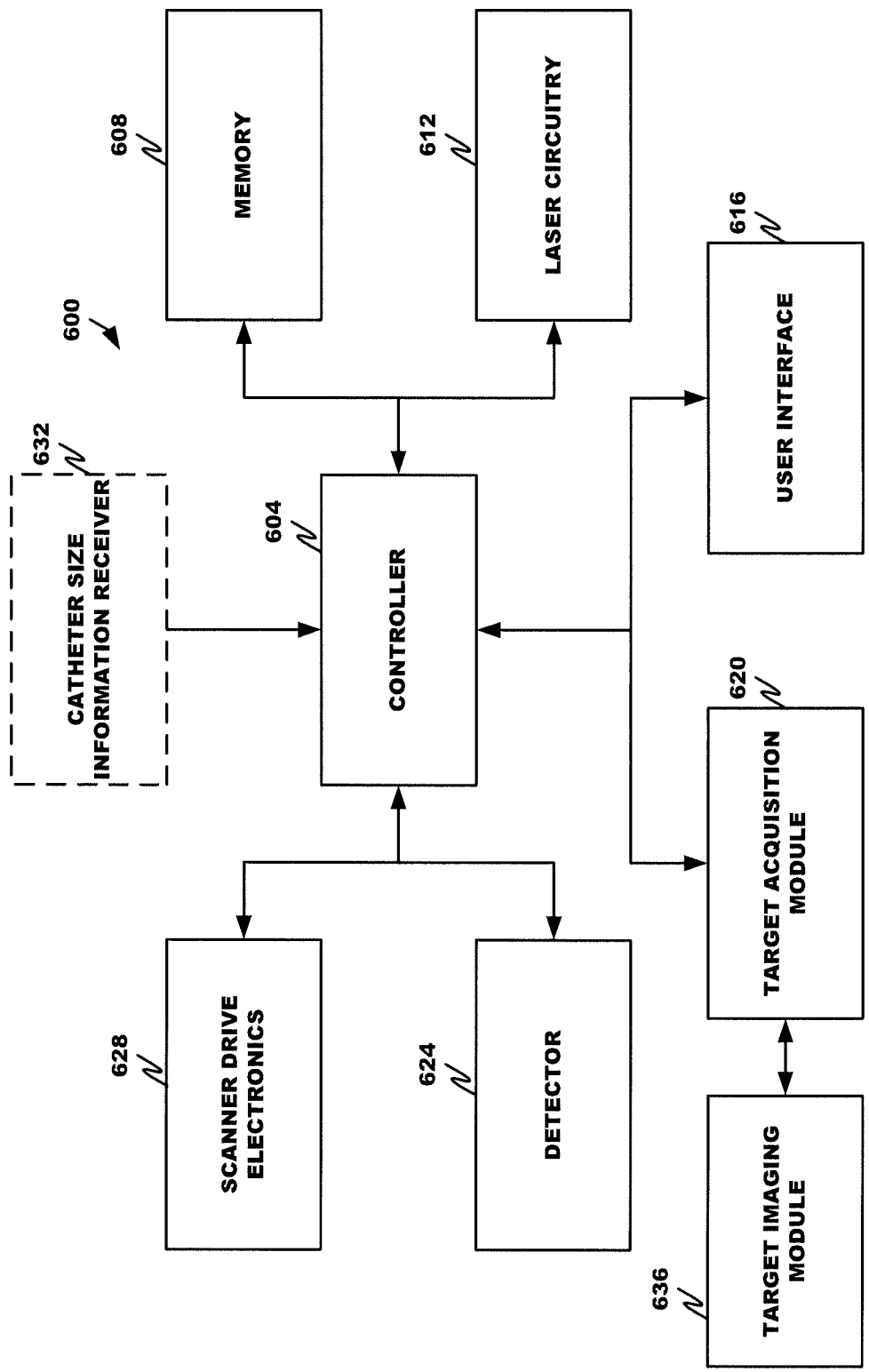
FIG. 6 is a block diagram of a control system according to an embodiment.

FIG. 6 depicts a control system 600 according to an embodiment. The control system 600 includes a controller 604 (which is typically a microprocessor) in signal and electrical communication with a memory 608, laser circuitry 612 to operate the laser 804, a user interface 616 to receive commands from and provide queries, target tissue or other endovascular structure information, and other feedback to a user, a target acquisition module 620 to determine target tissue or other endovascular structure location and/or characterization information, a detector 624 to select an optical channel from among plural optical channels for energization, scanner drive electronics 628 to operate the fiber selector 808 for energizing selected optical channels, and an optional catheter size information receiver 632 to receive information regarding the total fiber active area at the distal tip of the catheter. The controller 604 can use target tissue or other endovascular structure location and other imaging or diagnostic information, target tissue or other endovascular structure characterization information (such as tissue density, type, location, and configuration) and/or target tissue or other endovascular structure proximity to other non-target tissue structures, such as blood vessel walls, and total fiber active area at the distal end or tip to select not only laser parameters (such as, for each selected optical channel, fluence, energy density value, intensity, an active area, a maximum allowable fluence, a minimum allowable fluence, repetition rate (e.g., lasing on/off time), and lasing train time) but also the number of optical channels, the fiber active area for each optical channel, the fiber configuration for each optical channel, the specific optical channels to energize for target tissue ablation, and the sequence for energizing the selected channels.

The memory 608 can be any computer readable medium and stores, for a current catheterization procedure, a variety of information, including target tissue or other endovascular structure location, characterization information, target tissue or other endovascular structure proximity to non-target tissue structures and other imaging information, laser parameters, optical channel number and configuration, optical channel energizing sequence or ordering, patient information, total fiber active area of the distal end or tip, timestamps, and the like. It can also store various look up tables to enable the controller 604 to configure the optical channels for a currently connected catheter based on the total fiber active area of the catheter. Thus, different models or types or configurations of catheters having different total fiber active areas can have different numbers and configurations of optical channels.

Laser circuitry 612 enables operation of the laser by the controller 604 in response to user commands received by the user interface 616. The laser circuitry 612 is conventional.

The user interface 616 can be any audio, video, and/or tactile interface, such as a keyboard, display, microphone, and the like.

The target acquisition module 620 acquires imaging information via a target imaging (and/or diagnostic) module 636 (hereinafter referred to as target imaging module 636). The imaging information relates not only to the structure of the target tissue or other endovascular structure, such as an occlusion, unwanted tissue growth in proximity to a surgically implanted structure, and the like but also to non-target tissue structures in proximity to the target tissue structure. The target imaging module 636 can be any suitable imaging device, such as, but not limited to, laser induced fluorescence spectroscopy, optical coherence reflectometry, optical coherence tomography, and Raman spectroscopy. The imaging information can be a two, three, or four dimensional representation of the imaged tissue structures.

The detector 624 operatively engages the fiber selector 808 to determine a current optical channel positioned for energizing by the laser and/or a position of a selected optical channel relative to a desired position for the optical channel. The detector 624 can be any suitable configuration, whether a mechanical, optical, electrical, and/or electromagnetic device for tracking movement and/or a current position of the fiber selector 808. It can also be configured as one or more proximity sensors to fire the laser at the precise time that the beam is incident on the target fibers or bundles (or set) of fibers.

The scanner drive electronics 628 one or more of controllably directs the laser beam in a desired orientation and/or controls movement of the fiber selector 808. An example of the former configuration is described in U.S. Pat. No. 5,400,428 to Grace, which is incorporated herein by this reference. Grace discloses a dielectric mirror mounted on a galvanometer scanner that is moved to cause successive laser pulses to irradiate different optical channels, thereby enabling each fiber to receive radiation having sufficient fluence while reducing the energy per pulse (or the cw equivalent). Examples of the latter configuration are discussed below.

The catheter size information receiver 632 can be any configuration. For example, it can be based on a lookup table using an identifier of the catheter. The identifier can be provided by a pin sequence or configuration on the proximal end of the catheter. The sequence and/or configuration of pins is mounted to the proximal end of the catheter. The pin arrangement or sequence actuates switches in the catheter's coupler to generate a signal, which is forwarded to the controller 604. Using a lookup table in memory 608 and the signal, the controller 604 can identify the type and/or model of the catheter and therefore the appropriate catheter specifications, requirements, and other operating information. Each type and/or model of catheter has a unique pin sequence to actuate different switches for generating different signals. Other techniques for providing the identifier to the controller 604 may also be employed, such as the techniques discussed in copending U.S. patent application Ser. No. 13/804,812, filed concurrently herewith on Mar. 14, 2013, entitled "Intelligent Catheter", which is incorporated herein by reference in its entirety.

Various configurations of the fiber selector 808 will now be discussed with reference to FIGS. 4-5, 7A-B, and 9A-C. Although the fiber selector 808 is shown as being distal to the coupler, it may be positioned within or proximal to the coupler, depending on the application.

Figure 4:
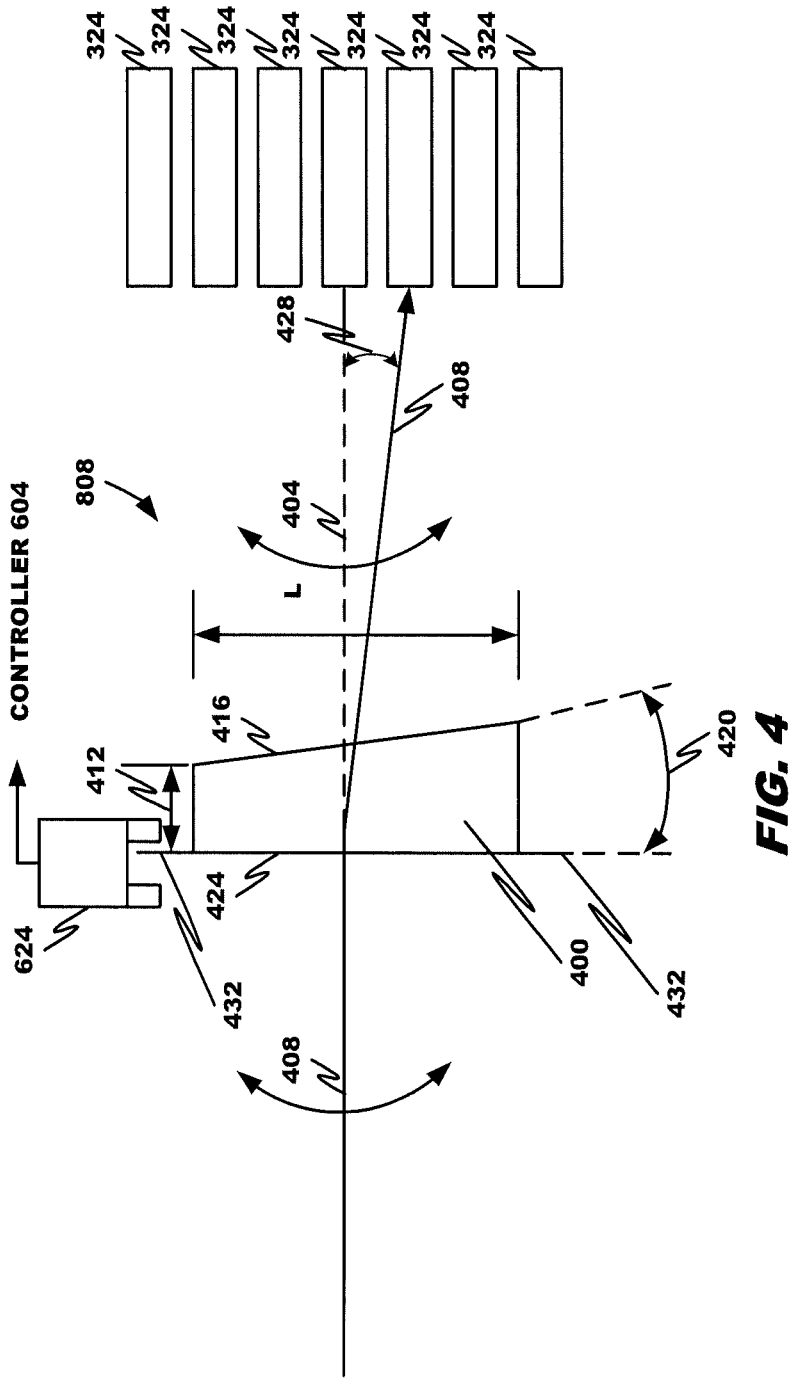
FIG. 4 is a block diagram of a multiplexed laser catheter according to an embodiment.

Referring to FIG. 4, a first fiber selector configuration is depicted. While FIG. 4 and other figures depict the optical fibers as a linear array for purposes of simplicity, it is to be understood that other fiber arrangements can be employed, particularly fibers oriented in a three dimensional array.

The fiber selector 808 comprises a rotating wedge optical member 400 positioned in the optical path 404 of the laser beam 408 to redirect, by optical refraction, the laser beam onto one or more selected fibers 324, with the optical fiber(s) irradiated at any one time corresponding to an optical channel and optical fiber(s) irradiated at different times corresponding to different optical channels. As will be appreciated, a wedge prism can be uncoated or coated with an anti-reflection coating and can deviate an angle of an incident beam. Typically, the wedge prism deviates the angle of the laser beam by an amount ranging from about 70 to about 20 degrees. The wedge optical member 400 typically has a thickness that is dependent upon the desired beam deviation, which is a also a function of the size of the coupler. This causes the laser beam 408 to be diverted at an angle $\Omega$428 relative to the optical path 404 along a diverging optical path. The motor-driven rotation of the optical member can be at fixed and/or variable speeds.

Alternatively, plural wedge optical members can be used to redirect the laser beam. For example, two wedge prisms can be used as an anamorphic pair to steer the beam anywhere within a circle described by the full angle 40, where $\theta$ is the deviation from a single prism. This beam steering is accomplished by rotating the two wedge prisms independently of each other.

The position of the wedge optical member 400 can be determined by the detector 624 based upon, for example, radiation reflected by a locating member 432, which rotates simultaneously and in an amount related to rotation of the wedge optical member 400. For example, the locating member 432 can be encoded with encoding elements that reflect light uniquely or substantially uniquely for any position around the circumference of the locating member 432. To produce the unique light reflectance can be the result of the encoding elements being differently sized, spaced, and/or colored. An example of such encoding elements is a bar code. The detector 624 emits light onto the locating member, detects the reflected spectra, and maps the reflected spectra against a lookup table that indexes each absolute and/or relative position around the locating member 432 against a corresponding set of reflected spectra. Based on the comparison, a locating signal is generated and sent to the controller 604, which then instructs a subcontroller (not shown), which further instructs the motor (not shown) to rotate the wedge optical member 400 a selected angle to align the selected optical channel with the redirected laser beam 408. By incorporating the optical encoder, the laser can be fired at the time the beam is deflected to the position to couple into the desired fiber or bundle of fibers. While tracking the position of the wedge optical member 400 is discussed with reference to an optical encoder, other types of encoders may be employed, such as mechanical, electrical, and/or electromagnetic position tracking devices.

Figure 5:
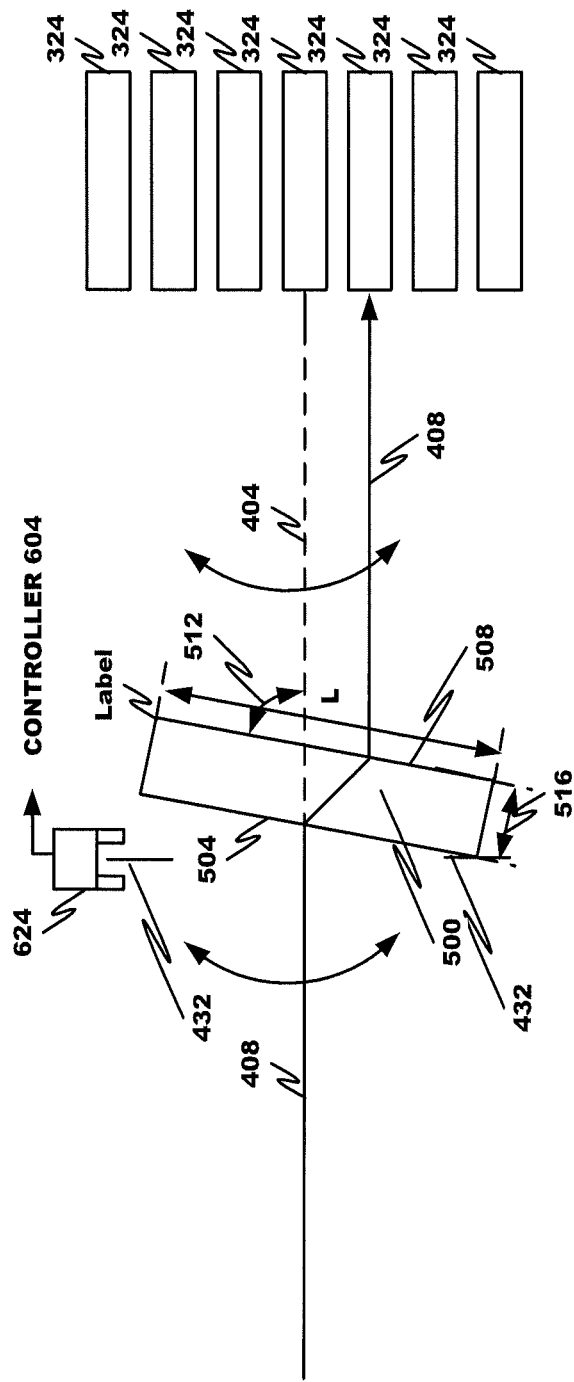
FIG. 5 is a block diagram of a multiplexed laser catheter according to an embodiment.

Referring to FIG. 5, a second fiber selector configuration is depicted.

The fiber selector 808 comprises a rotating parallel-faced optical member 500 positioned in the optical path 404 of the laser beam 408 to redirect, by optical refraction, the laser beam onto one or more selected fibers 324. The parallel-faced optical member 500 comprises opposing parallel faces 504 and 508 and is inclined relative to the optical path 404 at an angle $\delta$ 512 sufficient to deviate the laser beam 408 from the optical path 408 by an angle ranging from about 70 to about 20 degrees. The optical member 500 typically has a thickness that is dependent upon the desired beam deviation, which is a also a function of the size of the coupler. The inclined parallel surfaces 504 and 512 cause the laser beam 408 to be diverted and offset relative to and substantially parallel to the optical path 404.

In the first and second fiber selector configurations, the direction of rotation, whether clockwise, counterclockwise or both, is a matter of design choice.

In each of the first and second fiber selector configurations, complete rotation of the optical member causes the laser beam to trace, or define, a circle on the optical fibers. Partial rotation of the optical member causes the laser beam to trace a partial circle, with the length of the arc being proportional to the degree of rotation of the optical member. Any optical fiber positioned along the arc is irradiated by the incident redirected laser beam.

Other types of optical members may be used. For example, a faceted optical member, known as an axicon, may also be employed. In another example, a faceted optical element is employed.

Figure 7:
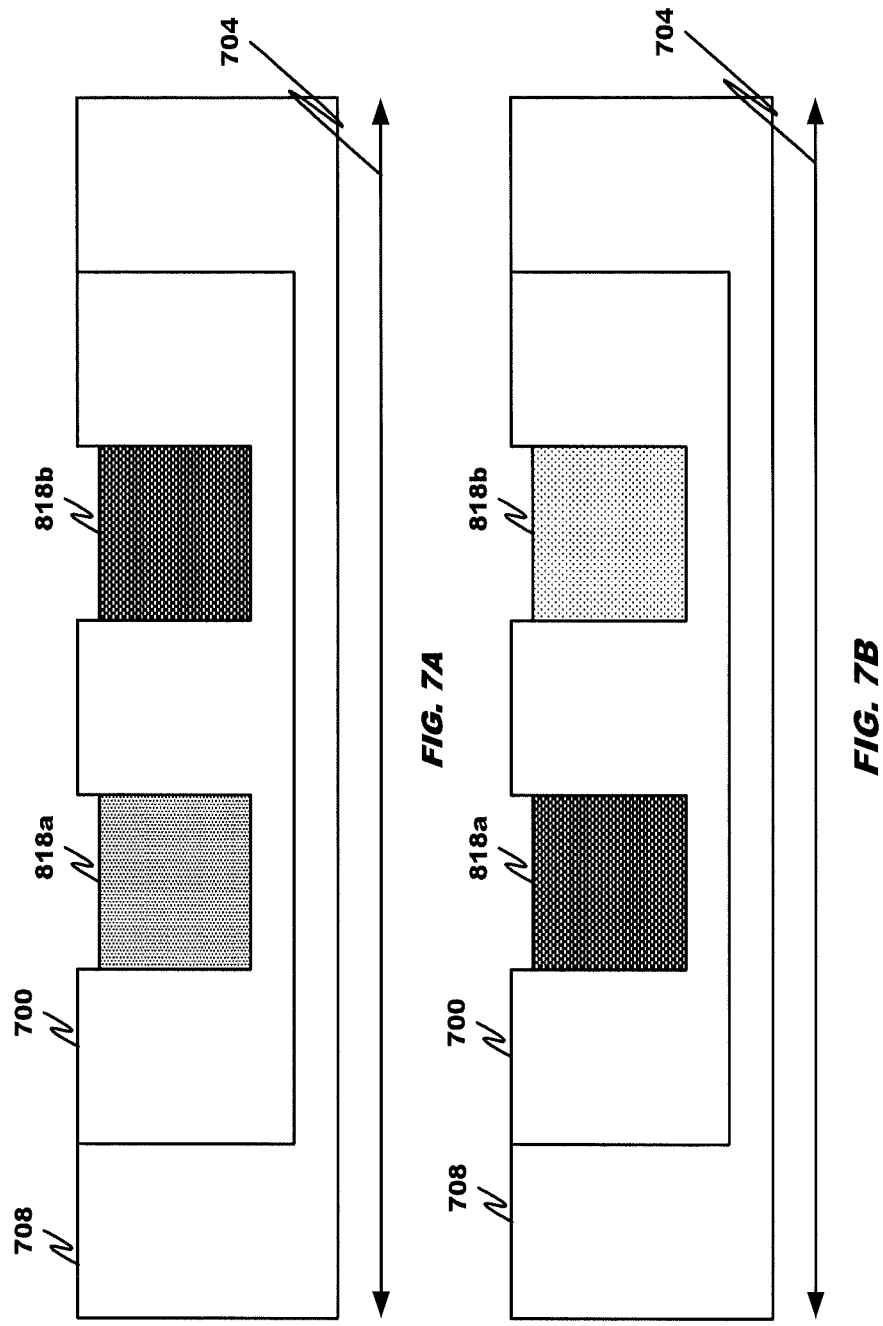
FIGS. 7A-B depict a fiber array according to an embodiment.

Referring to FIGS. 7A-B, a third fiber selector configuration is depicted. This configuration is further discussed in U.S. Pat. No. 5,400,428 referenced above.

A grooved fiber holder 700 holds two equally sized bundles of fibers 818a,b, each bundle corresponding to a different optical channel. Bundles 818a,b are centered upon the same linear transverse axis 704. The laser beam is focused so that the first incident beam pulse irradiates all of fiber bundle 818b (FIG. 7A), which is half of the total fibers. Either the beam or the fibers are then shifted so that next pulse of the laser beam is focused on bundle 818a (FIG. 7B). The grooved fiber holder 700 can be translated along the linear transverse axis 704 by displacing the holder 700 laterally in a carrier member 708, such as energizing a piezoelectric stack or a motor.

Figure 9:
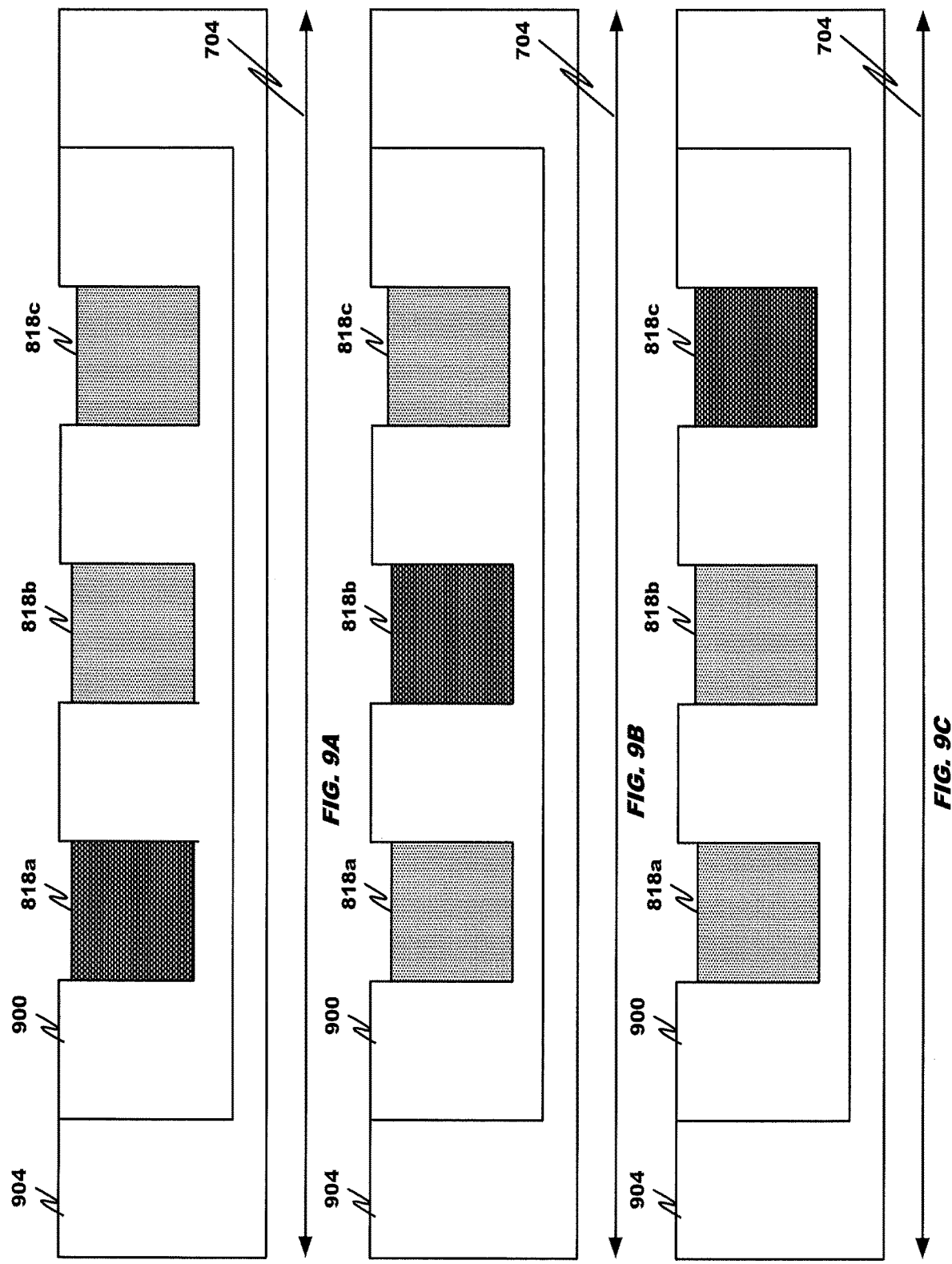
FIGS. 9A-C depict a fiber array according to an embodiment.

Referring to FIGS. 9A-C, a fourth fiber selector configuration is depicted. FIGS. 9A-C illustrate three bundles of optical fibers 818a, 818b and 818c, each bundle corresponding to a different optical channel. Each bundle of fibers 818a, 818b and 818c contains ⅓ of the total number of fibers. The optical fiber bundles are disposed in a grooved fiber holder 900 that moves laterally within a holder 904 as discussed above. First scan position (FIG. 9A) irradiates fiber bundle 818a. In a second scan position (FIG. 9B), the beam and fibers are moved relative to one another to irradiate the second fiber bundle 818b. In a third scan position (FIG. 9C), the next laser pulse is directed at the third bundle of optical fibers 818c. As in FIG. 5a, the fiber bundles are disposed in a linear manner along the same transverse axis 320 to provide for linear scanning.

As will be appreciated, other fiber selector configurations may be employed.

Regardless of the fiber selector configuration employed, the distal end or tip of the catheter energizes all or part of the laser emitters 108 as shown in FIGS. 11, 12A-B, 13A-C, and 14A-D. As noted, the portion of the laser emitters 108 energized, or the number of optical channels employed, depend on one or more of target tissue or other endovascular structure location, target tissue or other endovascular structure characterization information (such as tissue density, type, location, and configuration), current location and/or orientation of the distal tip of the catheter, and/or target tissue or other endovascular structure proximity to other non-target tissue structures, and total fiber active area at the distal end or tip. In FIGS. 11, 12A-B, 13A-C, and 14A-D, darkened laser emitters refer to those being energized while undarkened laser emitters refer to those not being energized.

FIG. 11 depicts a first operating mode in which all of the laser emitters 108 in the distal tip of the catheter are energized simultaneously.

FIGS. 12A-B depict a second operating mode for a 2-way multiplexing configuration in which one-half of the laser emitters 108 are energized simultaneously at a first time and the other half of the laser emitters 108 are energized simultaneously at a second (different) time. This operating mode can be produced by any of the first, second, and third fiber selector configurations.

FIGS. 13A-C depict a third operating mode for a 3-way multiplexing configuration in which a first one-third of the laser emitters 108 is energized simultaneously at a first time, a second one-third of the laser emitters 108 is energized simultaneously at a second time, and a third one-third of the laser emitters 108 is energized simultaneously at a third time. The first, second, and third times are different. This operating mode can be produced by any of the first, second, and fourth fiber selector configurations.

FIGS. 14A-D depict a fourth operating mode for a 4-way multiplexing configuration in which a first one-quarter of the laser emitters 108 is energized simultaneously at a first time, a second one-quarter of the laser emitters 108 is energized simultaneously at a second time, a third one-quarter of the laser emitters 108 is energized simultaneously at a third time, and a fourth one-quarter of the laser emitters 108 is energized simultaneously at a fourth time. The first, second, third, and fourth times are different. This operating mode can be produced by any of the first and second fiber selector configurations.

As will be appreciated, multiplexing may be performed up to N ways, with N being a whole number. Multiplexing is not limited to 2, 3, and 4 ways as shown in the above figures.

As will be further appreciated, the geometrical pattern of laser emitters 108 energized can be different from those shown. The laser emitters 108 can be energized along an arc, be randomly distributed, and/or be uniformly or nonuniformly distributed around the circumference of the distal tip of the catheter.

Figure 10:
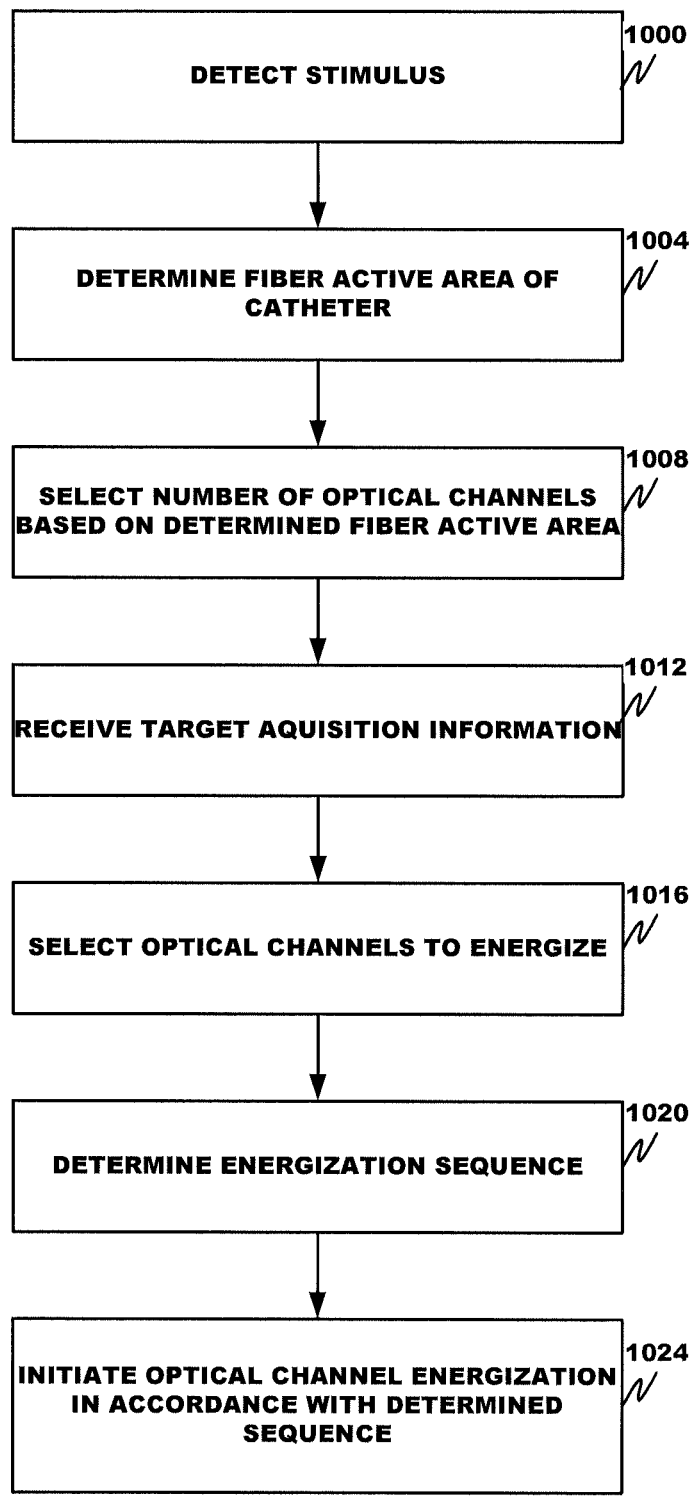
FIG. 10 depicts a control algorithm according to an embodiment.

An operation of the controller 604 will now be described with reference to FIG. 10.

The operation commences in step 1000 in which the controller 604 detects a stimulus. The stimulus can be, for example, a command received from an operator, such as a physician, via the user interface 616.

The controller 604 determines a total fiber active area of the catheter currently coupled to the coupler 812.

The controller 604, in step 1008, selects a number of optical channels based on the determined total fiber active area. As noted, this can be done using a lookup table. In other configurations, the controller 604 can use other information, particularly imaging information (including target tissue or other endovascular structure location, target tissue or other endovascular structure characterization information (such as tissue density, type, location, and configuration), current location and/or orientation of the distal tip of the catheter, and/or target tissue or other endovascular structure proximity to other non-target tissue structures) received from the target acquisition module 620 in addition to or lieu of the total fiber active area in selecting the number of optical channels. In that event, step 1008 would follow step 1012.

In one application, the controller 604 selects one or more of a fiber active area for each optical channel, a number of optical channels, a configuration of fibers in an optical channel, an optical channel to be irradiated, and an ordering of optical channel irradiation based on one or more of total fiber active area of the laser catheter, imaging information regarding the target and/or non-target endovascular structure(s), target endovascular structure characterization information, and current location and/or orientation of a distal tip of the laser catheter.

In step 1012, the controller 604 receives target acquisition information from the target acquisition module 620 and indirectly from the target imaging module 636. The target acquisition information is typically imaging information. In some configurations, additional wavelengths of light are launched down the fibers and through the laser emitters in the catheter and returned or reflected light analyzed to determine reflectivity and absorption data. This can be used to determine target and/or non-target tissue or other endovascular structure location, type, and/or contact area (area of contact between the distal tip and structure of the target tissue or other endovascular structure).

In step 1016, the controller 604 selects which of the optical channels to energize to ablate the target tissue or other endovascular structure. This can be determined based upon any or all of the information referenced in the prior paragraph and/or user input.

In step 1020, the controller 604 determines an energization sequence. The sequence governs which optical channels are energized and in what order and times. This can be determined based upon any or all of the information referenced previously including imaging information and user input.

In step 1024, the controller 604 initiates optical channel energization in accordance with the determined energization sequence.

The exemplary systems and methods of this disclosure have been described in relation to a laser catheter. However, to avoid unnecessarily obscuring the present disclosure, the preceding description omits a number of known structures and devices. This omission is not to be construed as a limitation of the scopes of the claims. Specific details are set forth to provide an understanding of the present disclosure. It should however be appreciated that the present disclosure may be practiced in a variety of ways beyond the specific detail set forth herein.

Furthermore, while the exemplary aspects, embodiments, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a base unit, or collocated on a particular node of a distributed network.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

For example, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:
receiving, at a microprocessor executable controller, catheter size information and a second information component, wherein the second information component comprises at least one of imaging information regarding a target endovascular structure, imaging information regarding a non-target endovascular structure, imaging information regarding target endovascular structure characterization information, a current location of a distal tip of the laser catheter, an orientation of the distal tip, an area of contact by the distal tip with the target endovascular structure, and an area of contact by the distal tip with the non-target endovascular structure,
upon receiving the catheter size information and the second information component, the microprocessor selecting at least one of a fiber active area for each optical channel, a number of optical channels, a configuration of fibers in an optical channel, an optical channel to be irradiated, and an ordering of optical channel irradiation;
directing a laser beam along an optical path onto a rotating optical member;
rotating the optical member to redirect the laser beam from the optical path onto one or more selected optical fibers of the laser catheter; and
irradiating, by the distal end of the laser catheter, the target endovascular structure.

2. The method of claim 1, wherein the microprocessor executable controller selects the number of optical channels and fiber active area per optical channel to maintain a level of energy delivered by the irradiated optical channel below an adverse effect threshold but above a level to provide a proper fluence value for tissue ablation.

3. The method of claim 1, wherein the microprocessor executable controller selects a first number of optical channels for a first catheter and a second number of optical channels for a second catheter and wherein the first and second numbers of optical channels are different and wherein a first total fiber active area of the first catheter is different from a second total fiber active area of the second catheter.

4. A system, comprising:
a microprocessor executable controller configured to:
receive catheter size information and a second information component, wherein the second information component comprises at least one of imaging information regarding a target endovascular structure, imaging information regarding a non-target endovascular structure, target endovascular structure characterization information, a current location of a distal tip of the laser catheter, an orientation of the distal tip, and an area of contact by the distal tip with the target endovascular structure, and an area of contact by the distal tip with the non-target endovascular structure;
select at least one of a fiber active area for each optical channel, a number of optical channels, a configuration of fibers in an optical channel, an optical channel to be irradiated, and an ordering of optical channel irradiation based on the catheter size information and the second information component; and
a rotating optical member to receive a laser beam along an optical path and rotate to a selected position to redirect the laser beam from the optical path onto one or more selected optical fibers of the laser catheter, wherein the distal end of the laser catheter irradiates the target endovascular structure.

5. The system of claim 4, wherein the microprocessor executable controller is configured to select the number of optical channels and fiber active area per optical channel to maintain a level of energy delivered by the irradiated optical channel below an adverse effect threshold but above a level to provide a proper fluence value for tissue ablation.

6. The system of claim 4, wherein the microprocessor executable controller is configured to select a first number of optical channels for a first catheter and a second number of optical channels for a second catheter, wherein the first and second numbers of optical channels are different, and wherein a first total fiber active area of the first catheter is different from a second total fiber active area of the second catheter.

7. A tangible, non-transient computer readable medium comprising microprocessor executable instructions that, when executed, perform operations comprising:
receiving catheter size information and a second information component, wherein the second information component comprises at least one of imaging information regarding a target endovascular structure, target endovascular structure characterization information, a current location of a distal tip of the laser catheter, an orientation of a distal tip of the laser catheter, and an area of contact by the distal tip with the target endovascular structure, and an area of contact by the distal tip with a non-target endovascular structure;
selecting at least one of a fiber active area for each optical channel, a number of optical channels, a configuration of fibers in an optical channel, an optical channel to be irradiated, and an ordering of optical channel irradiation based on the catheter size information and the second information component;
directing a laser beam along an optical path onto a rotating optical member;
rotating the optical member to redirect the laser beam from the optical path onto one or more selected optical fibers of the laser catheter; and
irradiating, by the distal end of the laser catheter, the target endovascular structure.

8. The computer readable medium of claim 7, wherein the instructions, when executed, select the number of optical channels and fiber active area per optical channel to maintain a level of energy delivered by the irradiated optical channel below an adverse effect threshold but above a level to provide a proper fluence value for tissue ablation.

9. The computer readable medium of claim 7, wherein the instructions, when executed, select a first number of optical channels for a first catheter and a second number of optical channels for a second catheter and wherein the first and second numbers of optical channels are different and wherein a first total fiber active area of the first catheter is different from a second total fiber active area of the second catheter.

* * * * *